US009944933B2

(12) United States Patent
Storici et al.

(10) Patent No.: US 9,944,933 B2
(45) Date of Patent: Apr. 17, 2018

(54) APTAMER-GUIDED GENE TARGETING

(71) Applicant: Georgia Tech Research Corporation, Atlanta, GA (US)

(72) Inventors: Francesca Storici, Smyrna, GA (US); Patrick Ruff, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 14/802,832

(22) Filed: Jul. 17, 2015

(65) Prior Publication Data
US 2016/0032292 A1 Feb. 4, 2016

Related U.S. Application Data

(60) Provisional application No. 62/025,744, filed on Jul. 17, 2014.

(51) Int. Cl.
| | |
|---|---|
| C12N 15/11 | (2006.01) |
| C12N 15/115 | (2010.01) |
| A61K 31/7088 | (2006.01) |
| A61K 31/711 | (2006.01) |

(52) U.S. Cl.
CPC ........ *C12N 15/115* (2013.01); *A61K 31/7088* (2013.01); *A61K 31/711* (2013.01); *C12N 15/111* (2013.01); *C12N 2310/11* (2013.01); *C12N 2310/16* (2013.01); *C12N 2310/3519* (2013.01); *C12N 2320/32* (2013.01)

(58) Field of Classification Search
CPC ... C12N 15/115; A61K 31/7088; A61K 45/06
See application file for complete search history.

(56) References Cited

U.S. PATENT DOCUMENTS

| | | | | |
|---|---|---|---|---|
| 6,111,095 A * | 8/2000 | Benseler | ................ | C07H 21/00 435/194 |
| 6,369,208 B1 * | 4/2002 | Cole | ...................... | C07H 21/00 435/196 |
| 6,833,252 B1 * | 12/2004 | Dujon | ........................ | 435/320.1 |
| 2006/0105975 A1 * | 5/2006 | Pendergrast | .......... | C12N 15/111 514/44 A |
| 2010/0291561 A1 * | 11/2010 | Milligan | ............... | C12N 15/111 435/6.1 |
| 2012/0014964 A1 * | 1/2012 | Baekelandt | .......... | A61K 38/005 424/158.1 |
| 2015/0089681 A1 * | 3/2015 | Van Der Oost | ........ | C12N 15/10 800/25 |
| 2017/0058298 A1 * | 3/2017 | Kennedy | .............. | C12N 15/113 |

OTHER PUBLICATIONS

Mondragon et al. Nucleic Acid Research 2015, 1:1-12.*
Straight to the target, using aptamers for gene targeting, bme.gatech/edu/bme/straight-target-using-aptamers-gene-targeting pp. 1-2. posted Feb. 6, 2014.*
Choulika et al. Molecular and Cellular Biology 1995 1968-1973.*
Allen, et al., "DNA-dependent protein kinase suppresses double-strand break-induced and spontaneous homologous recombination", PNAS, 99:3758-63 (2002).
Banga, et al., "Oligonucleotide-directed site-specific mutagenesis in *Drosophila melanogaster*", PNAS, 89:1735-9 (1992).
Berezovski, et al., "Thermochemistry of protein-DNA interaction studied with temperature-controlled nonequilibrium capillary electrophoresis of equilibrium mixtures", Anal. Chem., 77:1526-9 (2005).
Bertolini, et al., "Increased gene targeting in Ku70 and Xrcc4 transiently deficient human somatic cells", Mol. Biotech., 41:106-14 (2009).
Cowperthwaite, et al., "Bioinformatic analysis of the contribution of primer sequences to aptamer structures", J. Mol. Evol., 67:95-102 (2008).
David and Siewers, "Advances in yeast genome engineering", Fems Yeast Res., 15:1-14 (2015).
Di Primio, et al., "Potentiation of gene targeting in human cells by expression of *Saccharomyces cerevisiae* Rad52", Nucleic Acids Res., 33:4639-48 (2005).
Ellington and Szostak, "In vitro selection of RNA molecules that bind specific ligands", Nature, 346:818-22 (1990).
Fasullo, et al., "*Saccharomyces cerevisiae* rad51 mutants are defective in DNA damage-associated sister chromatid exchanges but exhibit increased rates of homology-directed translocations", Genetics, 158:959-72 (2001).
Katz, et al., "To nick or not to nick: comparison of I-SceI single- and double-strand break-induced recombination in yeast and human cells", PloS One, 9(2):e88840 (2014).
Keskin, et al., "Transcript-RBA-templated DNA recombination and repair", Nature, 515:436-9 (2014).
Lambert, et al., "Role of RAD51 in sister-chromatid exchanges in mammalian cells", Oncogene, 20:6627-31 (2001).
Legiewicz, et al., "Size, constant sequences, and optimal selection", RNA, 11:1701-9 (2005).
Lin, et at., "Creating a monomeric endonuclease TALE-I-SceI with high specificity and low genotoxicity in human cells", Nucleic Acids Res., 43(2):1112-22 (2015).
Nussbaum, et al., "Restriction-stimulated homologous recombination of plasmids by the RecE pathway of *Escherichia coli*", Genetics, 130:37-49 (1992).

(Continued)

*Primary Examiner* — Brian Whiteman
(74) *Attorney, Agent, or Firm* — Smith, Gambrell & Russell, LLP

(57) ABSTRACT

Compositions and methods for modifying genetic material are provided. One embodiment provides aptamers capable of binding to a site-specific DNA binding moiety to facilitate the exchange of homologous genetic information between a donor molecule and the desired target locus (aptamer-guided gene targeting or AGT). One embodiment provides an oligonucleotide containing a aptamer, preferably a DNA aptamer at the 5' end. The oligonucleotide also contains a region of homology, also referred to as donor DNA, to a desired nucleic acid, locus, or gene. The DNA binding moiety can be a nucleic acid, a protein, or a complex of proteins. In a preferred embodiment the DNA binding moiety is a homing endonuclease that cuts DNA to facilitate the modification of the DNA by the donor DNA.

10 Claims, 11 Drawing Sheets

(56) References Cited

OTHER PUBLICATIONS

Pan, et al., "The shorter the better: reducing fixed primer regions of oligonucleotide libraries for aptamer selection", Molecules, 14:1353-69 (2009).
Parsons, et al., "Precise binding of single-stranded DNA termini by human RAD52 protein", EMBO J., 19:4175-81 (2000).
Pierce, et al., "Ku DNA end-binding protein modulates homologous repair of double-strand breaks in mammalian cells", Genes Dev., 15:3237-42 (2001).
Porteus and Baltimore, "Chimeric nucleases stimulate gene targeting in human cells", Science, 300:763 (2003).
Potts, et al., "Human SMC5/6 complex promotes sister chromatid homologous recombination by recruiting the SMC1/3 cohesin complex to double-strand breaks", EMBO J., 25:3377-88 (2006).
Puchta, et al., "Homologous recombination in plant cells is enhanced by in vivo induction of double strand breaks into DNA by a site-specific endonuclease", Nucleic Acids Res., 21:5034-40 (1993).
Redden, et al., "The synthetic biology toolbox for tuning gene expression in yeast", Fems Yeast Res., doi: 10.1111/1567-1364.12188 (2015).
Roche, et al., "Finding the right partner in a 3D genome", Science, 342:1333-4 (2013).
Rouet, et al., "Expression of a site-specific endonuclease stimulates homologous recombination in mammalian cells", PNAS, 91:6064-8 (1994).
Ruff, et al., "Aptamer-guided gene targeting in yeast and human cells", Nucleic Acids Res., 42(7):e61 (2014).
Schcherbakova, et al., "Overexpression of bacterial RecA protein stimulates homologous recombination in somatic mammalian cells", Mutat. Res., 459:65-71 (2000).
Smith, et al., "Double-strand breaks at the target locus stimulate gene targeting in embryonic stem cells", Nucleic Acids Res., 23:5012-9 (1995).
Stafford, et al., "Three methods for optimization of cross-laboratory and cross-platform microarray expression data", Nucleic Acids Res., 35:e72 (2007).
Storici, et al., "Conservative repair of a chromosomal double-strand break by single-strand DNA through two steps of annealing", Mol. Cell. Biol., 26:7645-57 (2006).
Storici, et al., "RNA-templated DNA repair", Nature, 447:338-41 (2007).
Storici, et al., "Chromosomal site-specific double-strand breaks are efficiently targeted for repair by oligonucleotides in yeast", PNAS, 100:14994-9 (2003).
Stuckey, et al., "In vivo site-specific mutagenesis and gene collage using the delitto perfetto system in yeast *Saccharomyces cerevisiae*", Methods Mol. Biol., 745:173-191 (2011).
Tuerk and Gold, "Systematic evolution of ligands by exponential enrichment: RNA ligands to bacteriophage T4 DNA polymerase", Science 249:505-10 (1990).
Vasquez, et al., "Manipulating the mammalian genome by homologous recombination", PNAS, 98:8403-10 (2001).
Xiang, et al., "Aptamer-mediated cancer gene therapy", Curr Gene Ther., 15:109-19 (2015).
Xu, et al., "Nanocarriers in gene therapy: a review", J Biomed Nanotechnol., 10(12):3483-3507 Abstract Only (2014).
Yu and Gabriel, "Ku-dependent and Ku-independent end-joining pathways lead to chromosomal rearrangements during double-strand break repair in *Saccharomyces cerevisiae*", Genetics, 163:843-56 (2003).

\* cited by examiner

SEQUENCE LISTING

<160> NUMBER OF SEQ ID NOS: 50

<210> SEQ ID NO 1

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tagggataac agggtaat                                                 18

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Ala Gly Leu Ile Asp Ala Asp Gly
1               5

<210> SEQ ID NO 3
<211> LENGTH: 10
<212> TYPE: DNA
<213> ORGANISM: Homo sapiens

<400> SEQUENCE: 3
agaacaatgg                                                          10

<210> SEQ ID NO 4
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(55)
<223> OTHER INFORMATION: a, c, t, g, unknown or other

<400> SEQUENCE: 4
cttctgcccg cctccttccn nnnnnnnnn nnnnnnnnnn nnnnnnnnnn nnnnngacga    60
gataggcgga cact                                                     74

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cttctgcccg cctccttcc                                                19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agtgtccgcc tatctcgtc                                                19
```

<210> SEQ ID NO 7
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cttctgcccg cctccttccg gtcgggcaca cctgtcatac ccaatctcga ggccagacga    60
gataggcgga cact                                                     74

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acagtgctaa gtggatccgt actgtatgta catacagtac accgtattac cgccatgcat    60

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
attgagttcc taggatccgt actgtatgta catacagtac atctcggtct attcttttga    60

<210> SEQ ID NO 10
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caaaagaata gaccgagatg tactgtacat atgtacagta cggatctggt accttgtatt    60
a                                                                   61

<210> SEQ ID NO 11
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
taatacaagg taccagatcc gtactgtaca tatgtacagt acatctcggt ctattctttt    60
g                                                                   61

<210> SEQ ID NO 12
<211> LENGTH: 114
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 12
cttctgcccg cctccttccg cgggcgctgt tgacagcggt caggtggatg ggatggacga    60
gataggcgga cactggtttt gatgaagctg tcgcggatcc cacattctgg gaag          114

<210> SEQ ID NO 13
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
ggttttgatg aagctgtcgc ggatcccaca ttctgggaag cttctgcccg cctccttccg    60
cgggcgctgt tgacagcggt caggtggatg ggatggacga gataggcgga cact          114

<210> SEQ ID NO 14
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
cttctgcccg cctccttccg gtcgggcaca cctgtcatac ccaatctcga ggccagacga    60
gataggcgga cactggtttt gatgaagctg tcgcggatcc cacattctgg gaag          114

<210> SEQ ID NO 15
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gcgggcgctg ttgacagcgg tcaggtggat gggatgggaa aagggttttg atgaagctgt    60
cgcggatccc acattctggg aagacttcaa                                    90

<210> SEQ ID NO 16
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcgggcgctg ttgacagcgg tcaggtggat gggatgggtt ttgatgaagc tgtcgcggat    60
cccacattct gggaag                                                   76

<210> SEQ ID NO 17
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gcgggcgctg ttgacagcgg tcaggtggat gggatggtgg caagaatacc aagagttcct    60
cggtttgcca gttattaaaa gactcgtatt                                     90

<210> SEQ ID NO 18
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gcgggcgctg ttgacagcgg tcaggtggat gggatgggac attataccat tgatgcttgc    60
gtcacttctc aatttgaagc tcatttgaga                                     90

<210> SEQ ID NO 19
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gcgggcgctg ttgacagcgg tcaggtggat gggatgatac cattgatgct tgcgtcactt    60
ctcaatttga agctca                                                    76

<210> SEQ ID NO 20
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gcgggcgctg ttgacagcgg tcaggtggat gggatgcgct ttcatggccc tacaacatga    60
gccaccattg cctatttggt ccttggataa                                     90

<210> SEQ ID NO 21
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gcgggcgctg ttgacagcgg tcaggtggat gggatgatgg ccctacaaca tgagccacca    60
ttgcctattt ggtcct                                                    76

<210> SEQ ID NO 22
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttctgcccgc ctccttccga cgagataggc ggacacggaa aagggttttg atgaagctgt    60
cgcggatccc acattctggg aagacttcaa                                     90

<210> SEQ ID NO 23
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ttctgcccgc ctccttccga cgagataggc ggacacggtt ttgatgaagc tgtcgcggat    60
cccacattct gggaag                                                    76

<210> SEQ ID NO 24
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ttctgcccgc ctccttccga cgagataggc ggacacgtgg caagaatacc aagagttcct    60
cggtttgcca gttattaaaa gactcgtatt                                     90

<210> SEQ ID NO 25
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttctgcccgc ctccttccga cgagataggc ggacaccgct ttcatggccc tacaacatga    60
gccaccattg cctatttggt ccttggataa                                     90

<210> SEQ ID NO 26
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ttctgcccgc ctccttccga cgagataggc ggacacatgg ccctacaaca tgagccacca    60
ttgcctattt ggtcct                                                    76

<210> SEQ ID NO 27
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tgaaggccaa aacggctgaa tcgatagtgg aaaagggttt tgatgaagct gtcgcggatc    60
ccacattctg ggaagacttc aa                                             82

<210> SEQ ID NO 28
<211> LENGTH: 40
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 28
ggttttgatg aagctgtcgc ggatcccaca ttctgggaag                           40

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
atggccctac aacatgagcc accattgcct atttggtcct                           40

<210> SEQ ID NO 30
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gcgggcgctg ttgacagcgg tcaggtggat gggatggcga ccgtgaccca ggactcctcc     60
ctgcaggacg gctgcttcat ctacaaggtg                                      90

<210> SEQ ID NO 31
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gcgggcgctg ttgacagcgg tcaggtggat gggatgtgac ccaggactcc tccctgcagg     60
acggctgctt catcta                                                     76

<210> SEQ ID NO 32
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcgggcgctg ttgacagcgg tcaggtggat gggatgcagg actcctccct gcaggacggc     60
tgcttc                                                                66

<210> SEQ ID NO 33
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ttctgcccgc ctccttccga cgagataggc ggacacgcga ccgtgaccca ggactcctcc     60

```
ctgcaggacg gctgcttcat ctacaaggtg                                              90

<210> SEQ ID NO 34
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ttctgcccgc ctccttccga cgagataggc ggacactgac ccaggactcc tccctgcagg            60
acggctgctt catcta                                                            76

<210> SEQ ID NO 35
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ttctgcccgc ctccttccga cgagataggc ggacaccagg actcctccct gcaggacggc            60
tgcttc                                                                       66

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tgacccagga ctcctccctg caggacggct gcttcatcta                                  40

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
caggactcct ccctgcagga cggctgcttc                                             30

<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tcagttcctt ggttagg                                                           17

<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 39
tctaagactt gtgagtcata cggtgggacg cggtaa                                36

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tgaaggccaa aacggctgaa tcgatagt                                         28

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gccttgcttg aactggtagc acatgt                                           26

<210> SEQ ID NO 42
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ctcctggtct agacgagcct cactttccaa atcatgacga gataggcgga c               51

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gcgggcgctg ttgacagcgg tcaggtggat gggatg                                36

<210> SEQ ID NO 44
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ctgcatttcc tatggacaca gtgcttcgtt caatc                                 35

<210> SEQ ID NO 45
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gagtgccgcg ggggactgtc aagtcgctgg gtcta                        35

<210> SEQ ID NO 46
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
aggcagacgc ctctgacgca aggtgcattg cctttt                       35

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
atgtgtattt gccagtaa                                           18

<210> SEQ ID NO 48
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gttgcgctct agctgatcgt gtttatccca aaggca                       36

<210> SEQ ID NO 49
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cttctgcccg cctccttccg cgggcgctgt tgacagcggt caggtggatg ggatggacga    60
gataggcgga cact                                               74

<210> SEQ ID NO 50
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ccgcctcctt ccgcgggcgc tgttgacagc ggtcaggtgg atgggatgga cgagataggc    60
gg                                                            62

US 9,944,933 B2

APTAMER-GUIDED GENE TARGETING

CROSS REFERENCE TO RELATED PATENTS

This application claims benefit of and priority to U.S. Provisional Patent Application No. 62/025,744 filed on Jul. 17, 2014, and which is incorporated by reference herein in its entirety.

STATEMENT REGARDING FEDERALLY SPONSORED RESEARCH OR DEVELOPMENT

This invention was made with government support under grant number R21EB9228 awarded by the National Institutes of Health. The government has certain rights in the invention.

FIELD OF THE INVENTION

The invention is generally directed to molecular biology and gene editing.

REFERENCE TO SEQUENCE LISTING

The instant application contains a Sequence Listing which has been submitted electronically in ASCII format and is hereby incorporated by reference in its entirety. Said ASCII copy, created on Sep. 10, 2015, is named GTRC_6757_SL.txt and is 14,128 bytes in size.

BACKGROUND OF THE INVENTION

Targeted gene modification is a powerful tool for researchers interested in functional analysis of genes and potentially for gene therapy applications. The primary limitation of gene targeting is the low frequency with which it occurs in many organisms and cell types, including mammalian cells, occurring in roughly one cell for every $10^5$-$10^7$ treated cells (Vasquez, et al., *Proc. Natl Acad. Sci. USA*, 98:8403-8410 (2001)). The low frequency of gene targeting, which relies on HR is due in part to the much higher frequency of random integration via nonhomologous end joining (NHEJ), which occurs in about 1 cell for every $10^2$-$10^4$ treated cells (Vasquez, et al., *Proc. Natl Acad. Sci. USA*, 98:8403-8410 (2001)).

Several strategies have been used to increase the frequency of gene targeting. It was shown that a DNA double-strand break (DSB) at the target site increases the frequency of gene targeting several orders of magnitude in bacteria (Nussbaum, et al., *Genetics*, 130:37-49 (1992)), yeast (Storici, et al., *Proc. Natl Acad. Sci. USA*, 100:14994-14999 (2003)), plants (Puchta, et al., *Nucleic Acids Res.*, 21:5034-5040 (1993)), fruit flies (Banga, et al., *Proc. Natl Acad. Sci. USA*, 89:1735-1739 (1992)), mice (Rouet, et al., *Proc. Natl Acad. Sci. USA*, 91:6064-6068 (1994)), human embryonic stem cells (Smith, et al., *Nucleic Acids Res.*, 23:5012-5019 (1995)) and many other cell types. Another strategy to increase gene targeting in mammalian cells has been achieved through the overexpression of key recombination proteins from HR proficient organisms. Overexpression of bacterial RecA led to a 10-fold increase in gene targeting in mouse cells (Schcherbakova, et al., *Mutat. Res.*, 459:65-71 (2000)); likewise, overexpression of yeast Rad52 led to a 37-fold increase in gene targeting in human cells (Di Primio, et al., *Nucleic Acids Res.*, 33:4639-4648 (2005)). Conversely, another approach for increasing gene targeting in human cells involves decreasing the amount of DSB repair through the pathway of NHEJ. In mouse embryonic stem cells, an increase in gene targeting was seen in Ku70 (6-fold), XRCC4 (2-fold) and DNAPK-cs-deficient cell lines (2-fold) (Pierce, et al., *Genes Dev.*, 15:3237-3242 (2001)), and a 3-fold increase in Chinese hamster ovary cells lacking DNAPK-cs (Allen, et al., *Proc. Natl Acad. Sci. USA*, 99:3758-3763 (2002)). Similarly, knockdown of Ku70 and XRCC4 in human colon cancer cells led to a 30-fold increase in gene targeting (Bertolini, et al., *Mol. Biotech.*, 41:106-114 (2009)). Different from the methodologies mentioned above that focused on increasing HR or decreasing NHEJ, it was shown that knockout of the RAD51 recombinase prevents DSB-induced sister chromatid exchange (Fasullo, et al., *Genetics*, 158:959-972 (2001)), and thus facilitates gene targeting by single-stranded oligonucleotides at the site of a DSB in both haploid and diploid yeast systems (Storici, et al., *Mol. Cell. Biol.*, 26:7645-7657 (2006)). Gene correction close to a DSB by single-stranded oligonucleotides does not require Rad51, but only the strand annealing function of Rad52 (Storici, et al., *Mol. Cell. Biol.*, 26:7645-7657 (2006)). Thus, deleting Rad51 favours DSB-driven recombination by oligonucleotides by strongly reducing the competition with the sister chromatid and/or the homologous chromosome for DSB repair (Fasullo, et al., *Genetics*, 158:959-972 (2001); Storici, et al., *Mol. Cell. Biol.*, 26:7645-7657 (2006); Lambert, et al., *Oncogene*, 20:6627-6631 (2001)). Similarly, it was shown that by knocking down human SMC1, important for HR between sister chromatids, gene targeting increases (Potts, et al., *EMBO J.*, 25:3377-3388 (2006)). Without proximity to the DSB site, the sister chromatid was used less frequently as a donor, shifting repair of the DSB more towards HR with the exogenous donor sequence Therefore, it is an object of the invention to provide improved compositions and methods for modifying genetic material.

It is another object of the invention to provide methods and compositions for gene therapy.

It is still another object of the invention to provide compositions and methods for targeting oligonucleotides to the specific sites in the genome.

SUMMARY OF THE INVENTION

Compositions and methods for modifying genetic material are provided. One embodiment provides aptamers capable of binding to a site-specific DNA binding moiety to facilitate the exchange of homologous genetic information between a donor molecule and the desired target locus (aptamer-guided gene targeting or AGT). One embodiment provides an oligonucleotide containing a aptamer, preferably a DNA aptamer at the 5' end. The oligonucleotide also contains a region of homology, also referred to as donor DNA, to a desired nucleic acid, locus, or gene. The DNA binding moiety can be a nucleic acid, a protein, or a complex of proteins. In a preferred embodiment the DNA binding moiety is a homing endonuclease that cuts DNA to facilitate the modification of the DNA by the donor DNA. The DNA binding moiety can be naturally occurring or genetically engineered to bind to and cut a desired nucleic acid sequence at a specific site or locus. The aptamer containing oligonucleotides are generally referred to herein as "bifunctional oligonucleotides".

Generally, the bifunctional oligonucleotides are transformed or transfected into the cell to modify a target locus in the genome of the cell. The aptamer binds to a DNA binding moiety either in the cytoplasm, nucleus, or mitochondria. The DNA binding moiety then directs the bifunctional oligonucleotide to the targeted locus. In certain embodiments, the bifunctional oligonucleotide binds to a DNA binding moiety that directs the bifunctional oligonucleotide to the mitochondrial DNA. In a preferred embodiment the DNA binding moiety generates a doublestranded break (DSB) at the targeted locus. Resection of the 5' ends of the DSB gives rise to single-stranded 3' DNA tails. The 3' tail of the bifunctional oligonucleotide anneals to its complementary DNA sequence on the targeted locus. After the non-homologous sequence is clipped, DNA synthesis proceeds on the template sequence. After unwinding of the bifunctional oligonucleotide, a second annealing step occurs between the extended 3' end and the other 3' end generated from the DSB. Further processing, gap-filling DNA synthesis, and subsequent ligation complete repair and modification of the target locus.

The bifunctional oligonucleotides can be encoded by a vector. The vector can be used to transfect or transform cells needing genetic modification. The vector can also encode the DNA binding moiety.

Another embodiment provides a method for correcting a genetic defect in a subject by administering one or more bifunctional oligonucleotides that contain a region of homology to the gene or locus to be modified, wherein the bifunctional oligonucleotide contains an aptamer specific for a homing endonuclease.

Figures 6A, 6O:
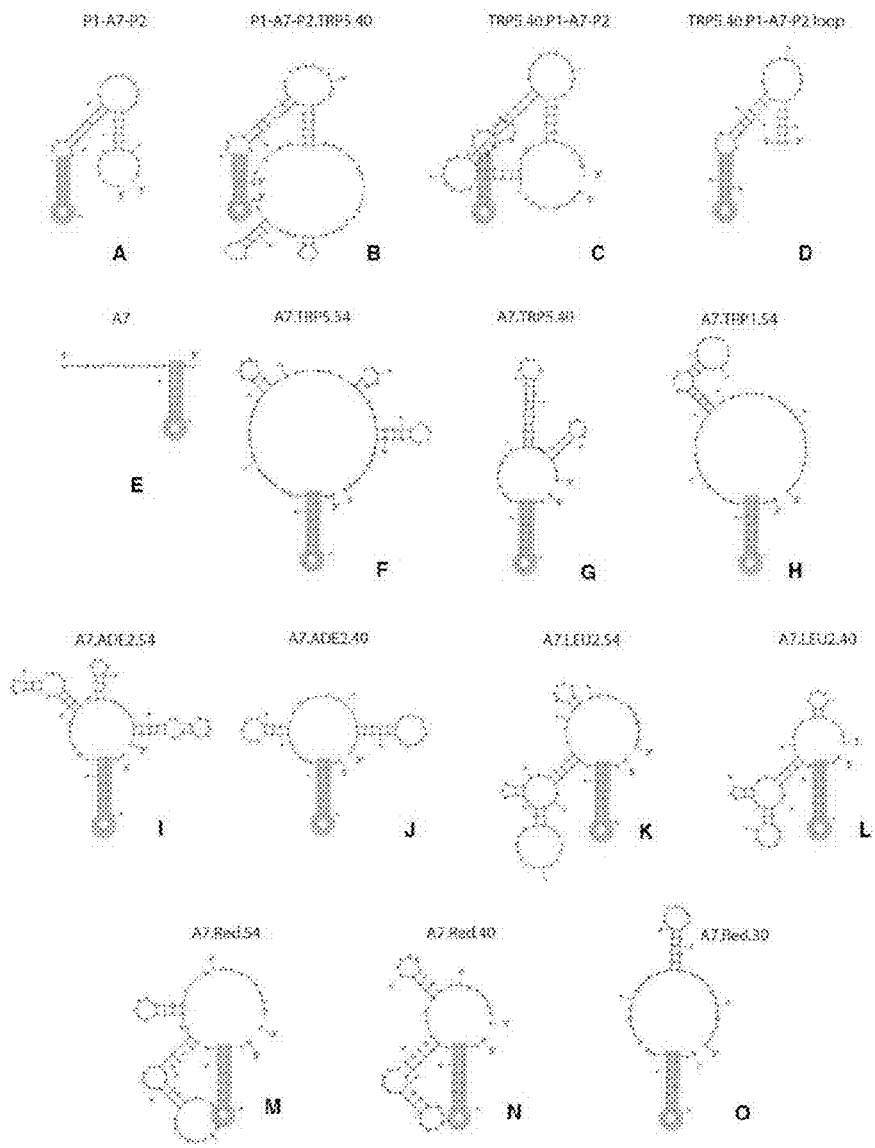

FIGS. 6A-6O show the predicted secondary structure of oligonucleotides containing the I-SceI aptamer. Lowest free-energy secondary structures predicted for the oligonucleotides used in yeast and human cells containing the A7 aptamer sequence (aptamer hairpin highlighted in green). (6A) The A7 aptamer with primers P1 and P2 from the random DNA library (SEQ ID NO: 49). (6B) P1-A7-P2.TRP5.40 oligonucleotide (SEQ ID NO: 12). (6C) The TRP5.40.P1-A7-P2 oligonucleotide (SEQ ID NO: 13). (6D) The aptamer loop from (6C), which was obscured by the overlapping stem-loop (SEQ ID NO: 50). (6E) The A7 aptamer without primers from the random DNA library (SEQ ID NO: 43). (6F) The A7.TRP5.54 oligonucleotide (SEQ ID NO: 15). (6G) The A7.TRP5.40 oligonucleotide (SEQ ID NO: 16). (6H) The A7.TRP1.54 oligonucleotide (SEQ ID NO: 17). (6I) The A7.ADE2.54 oligonucleotide (SEQ ID NO: 18). (6J) The A7.ADE2.40 oligonucleotide (SEQ ID NO: 19). (6K) The A7.LEU2.54 oligonucleotide (SEQ ID NO: 20). (6L) The A7.LEU2.40 oligonucleotide (SEQ ID NO: 21). (6M) The A7.Red.54 oligonucleotide (SEQ ID NO: 30). (6N) The A7.Red.40 oligonucleotide (SEQ ID NO: 31). (6O) The A7.Red.30 oligonucleotide (SEQ ID NO: 32).

Figure 7:
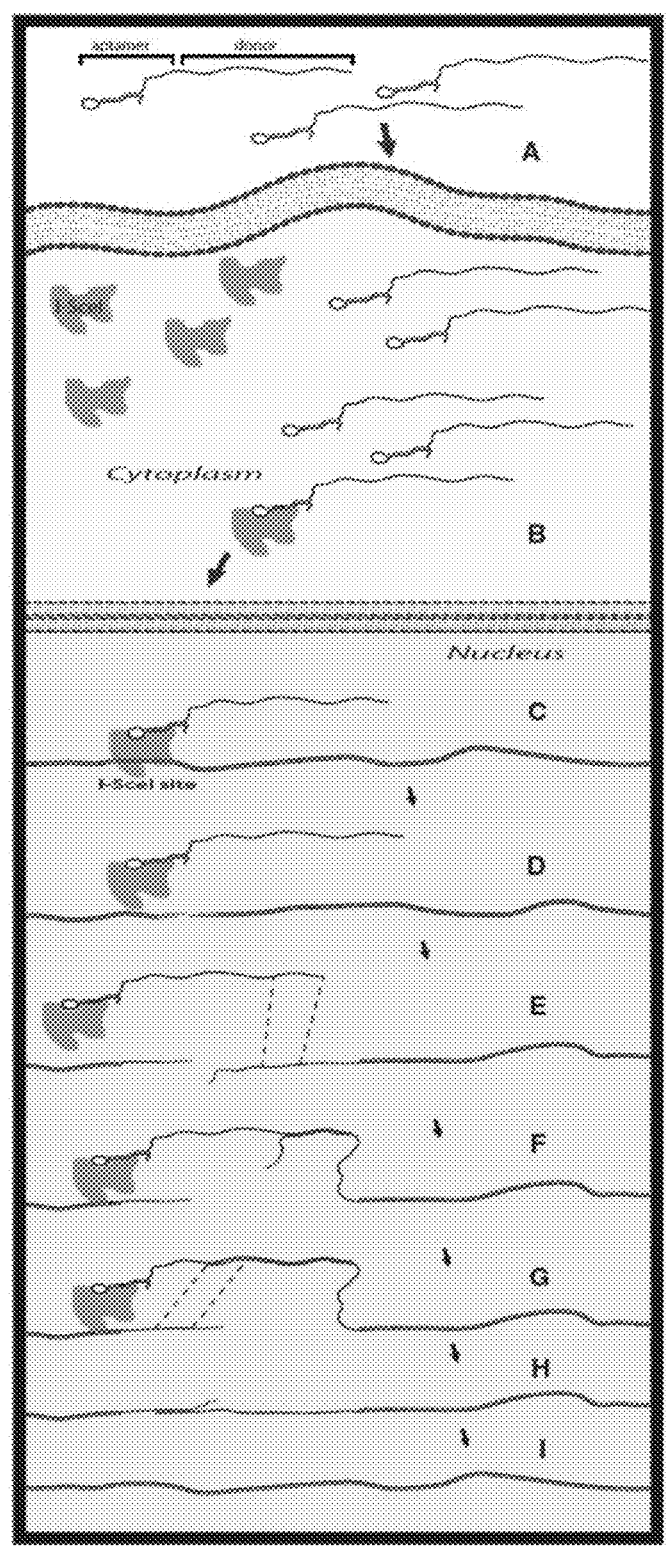

FIG. 7 shows an aptamer-guided gene targeting model. (A) Bifunctional-targeting oligonucleotides containing the A7 aptamer at the 5' end along with a region of homology to restore the function of a defective gene of interest are transformed/transfected into the cell. The I-SceI endonuclease is produced from the chromosome (yeast) or from a transfected expression vector (humans). (B) The A7 aptamer then binds to the I-SceI protein, either in the cytoplasm (shown here) or in the nucleus. (C) I-SceI drives the bifunctional oligonucleotide to the targeted locus containing the I-SceI site, and (D) generates a DSB at the I-SceI site. (E) Resection of the 5' ends of the DSB gives rise to single-stranded 3' DNA tails. (F) The 3' tail of the bifunctional oligonucleotide anneals to its complementary DNA sequence on the targeted DNA, and after the non-homologous sequence is clipped, (G) DNA synthesis proceeds on the template sequence. (H) After unwinding of the bifunctional oligonucleotide, a second annealing step occurs between the extended 3' end and the other 3' end generated from the DSB. (I) Further processing, gap-filling DNA synthesis, and subsequent ligation complete repair and modification of the target locus.

Figures 8A, 8B:
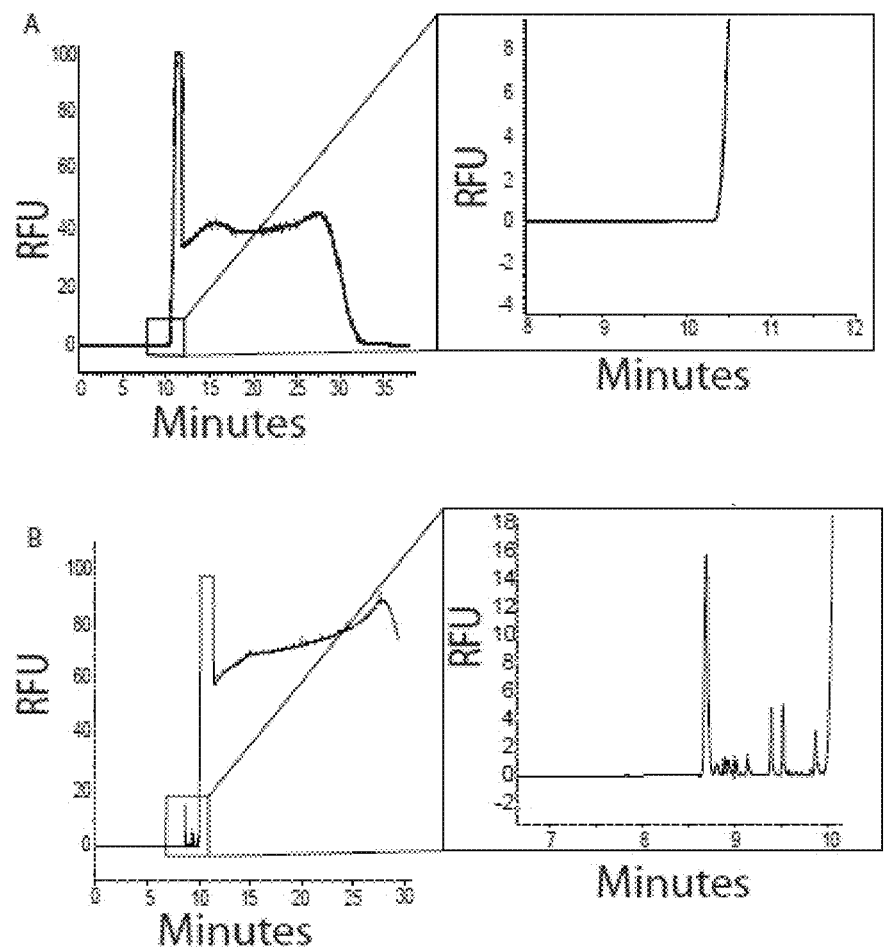

FIGS. 8A and 8B show CE electropherograms of a DNA library run without I-SceI protein and the bulk affinity assay with I-SceI showing key steps of the aptamer selection, the X axis shows the time each sample took to reach the detector and the Y axis shows the amount of DNA measured by the relative fluorescence units (RFU). (8A) The random single-stranded DNA library (1 µM) was run in the absence of I-SceI. The free DNA begins to appear at approximately 10 minutes. The relative fluorescence units (RFU) measure the amount of the FAM-labeled DNA. There are no complexes prior to 10 minutes, as shown in a zoomed-in picture displayed in the box to the right. (8B) An initial bulk affinity assay was performed with 1.5 µM I-SceI and 100 nM DNA in order to view any I-SceI-DNA complexes. I-SceI-DNA complexes were observed prior to the free DNA peak at ~10 minutes. A zoomed-in picture of the complexes is displayed in the box to the right.

FIGS. 9A-9D show a series of CE runs showing the first 3 rounds of selection, as well as the CE run of the A7 aptamer with I-SceI. The X axis shows the time each sample took to reach the detector and the Y axis shows the amount of DNA measured by the relative fluorescence units (RFU). (9A) In the first round of selection, I-SceI-DNA complex peaks could be detected prior to the free DNA peak at ~10 minutes. A zoomed-in picture of the complexes is displayed in the box to the right. The second round of selection was done using the complexes collected in the first round of selection. (9B) For round 2, the amount of total DNA drastically decreased while the ratio of DNA in complex with I-SceI compared to the total DNA increased. (9C) In the third round of selection the amount of total DNA was very low, and no complex could be detected. (9D) One of the selected aptamers, A7, run with I-SceI. 50 nM PAGE purified, FAM-labeled A7 was run with 1 µM of dialyzed I-SceI. The I-SceI-DNA complex formed with I-SceI is boxed and the unbound DNA is boxed with dotted lines. Due to the single-stranded nature of the DNA sequence, there is a broad peak for the unbound DNA not complexed with I-SceI due to self hybridization and concatenation between the oligonucleotides.

Figure 10:
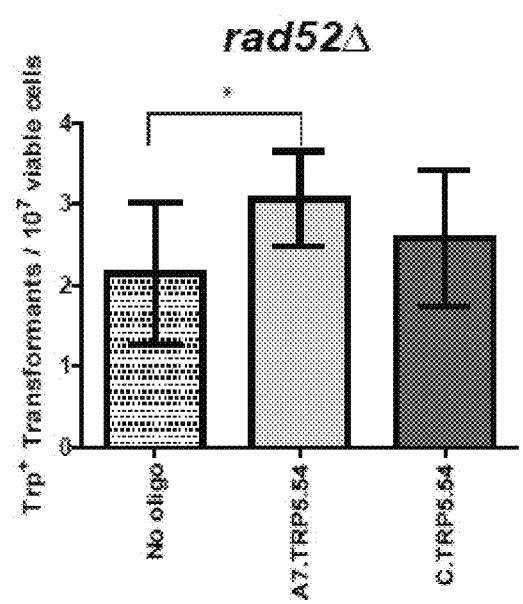

FIG. 10 is a bar graph showing aptamer-guided gene targeting is Rad52 dependent. Frequency of gene correction by the aptamer-containing oligonucleotide (A7.TRP5.54 shown in light gray) or the non-binding control oligonucleotide (C.TRP5.54 shown in dark gray) (X axis) was measured by the number of Trp+ transformants per $10^7$ viable cells (Y axis) in a rad52 Δ FRO-155 (T5B) background strain. Bars correspond to the mean value and error bars represent 95% confidence intervals. Asterisks denote statistical significant difference between the aptamer containing oligonucleotide and the no oligonucleotide negative control (* for p<0.05,  for p<0.01, * for p<0.001, and **** for p<0.0001).

DETAILED DESCRIPTION OF THE INVENTION

I. Definitions

Unless defined otherwise, all technical and scientific terms used herein have the same meaning as commonly understood by one of ordinary skill in the art. Although any methods and materials similar or equivalent to those described herein can be used in the practice or testing of the present invention, the preferred methods and materials are described.

An "aptamer" refers to a nucleic acid molecule that is capable of binding to a particular molecule of interest with high affinity and specificity (Tuerk and Gold, Science 249: 505 (1990); Ellington and Szostak, Nature 346:818 (1990)). The binding of a ligand to an aptamer, which is typically RNA, changes the conformation of the aptamer and the nucleic acid within which the aptamer is located. The conformation change inhibits translation of an mRNA in which the aptamer is located, for example, or otherwise interferes with the normal activity of the nucleic acid. Aptamers may also be composed of DNA or may comprise nonnatural nucleotides and nucleotide analogs. An aptamer will most typically have been obtained by in vitro selection for binding of a target molecule. However, in vivo selection of an aptamer is also possible.

Aptamers have specific binding regions which are capable of forming complexes with an intended target molecule in an environment wherein other substances in the same environment are not complexed to the nucleic acid. The specificity of the binding is defined in terms of the comparative dissociation constants (Kd) of the aptamer for its ligand as compared to the dissociation constant of the aptamer for other materials in the environment or unrelated molecules in general. Typically, the Kd for the aptamer with respect to its ligand will be at least about 10-fold less than the Kd for the aptamer with unrelated material or accompanying material in the environment. Even more preferably, the Kd will be at least about 50-fold less, more preferably at least about 100-fold less, and most preferably at least about 200-fold less.

An aptamer will typically be between about 10 and about 300 nucleotides in length. More commonly, an aptamer will be between about 30 and about 100 nucleotides in length.

The terms "nucleic acid molecule" and "oligonucleotide" and "polynucleotide" refer to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues. Also included are molecules having naturally occurring phosphodiester linkages as well as those having non-naturally occurring linkages, e.g., for stabilization purposes. The nucleic acid may be in any physical form, e.g., linear, circular, or supercoiled. The term nucleic acid is used interchangeably with oligonucleotide, gene, cDNA, and mRNA encoded by a gene.

The term "gene" is used broadly to refer to any segment of DNA associated with a biological function. Thus, genes include coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

An "exogenous DNA" or a "transgene," refers to a gene that originates from a source foreign to the particular host cell, or, if from the same source, is modified from its original form. Thus, a transgene in a host cell includes a gene that is endogenous to the particular host cell, but has been modified in some manner. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

The term "naturally-occurring" is used to describe an object that can be found in nature as distinct from being artificially produced by man. For example, a polypeptide or polynucleotide sequence that is present in an organism (including viruses) that can be isolated from a source in nature and which has not been intentionally modified by man in the laboratory is naturally-occurring.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

A DNA segment is "operably linked" when placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers, for example, need not be contiguous with the coding sequences whose transcription they control Linking is accomplished by ligation at convenient restriction sites or at adapters or linkers inserted in lieu thereof.

"Promoter" refers to a region of DNA involved in binding the RNA polymerase to initiate transcription. An "inducible promote" refers to a promoter that directs expression of a gene where the level of expression is alterable by environmental or developmental factors such as, for example, temperature, pH, transcription factors and chemicals. The term "constitutive promoter" refers to a promoter that is active under most environmental and developmental conditions.

An "expression cassette" is a nucleic acid construct, generated recombinantly or synthetically, with nucleic acid elements that are capable of effecting expression of a gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "vector" refers to a composition for transferring a nucleic acid (or nucleic acids) to a host cell. A vector comprises a nucleic acid encoding the nucleic acid to be transferred, and optionally comprises a viral capsid or other materials for facilitating entry of the nucleic acid into the host cell and/or replication of the vector in the host cell (e.g., reverse transcriptase or other enzymes which are packaged within the capsid, or as part of the capsid).

The term "viral vector" refers to a vector that comprises a viral nucleic acid and can also include a viral capsid and/or replication function.

The term "expression vector" refers to a vector which comprises some or all of the following elements operably linked at appropriate distance for allowing functional gene expression: replication origin, promoter, enhancer, 5' mRNA leader sequence, ribosomal binding site, nucleic acid cassette, selectable marker sequences, and termination and polyadenylation sites. One or more of these elements may be omitted in specific applications. The nucleic acid cassette can include a restriction site for insertion of the nucleic acid sequence to be expressed. In a functional vector the nucleic acid cassette contains the nucleic acid sequence to be expressed including translation initiation and termination sites. An expression vector is constructed so that the particular coding sequence is located in the vector with the appropriate regulatory sequences, the positioning and orientation of the coding sequence with respect to the control sequence being such that the coding sequence is transcribed under the "control" of the control sequence. Modification of the sequences encoding the particular protein of interest may be desirable to achieve this end. For example, in some cases it may be necessary to modify the sequence so that it may be attached to the control sequences with the appropriate orientation, or to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site which is in reading frame with and under regulatory control of the control sequences.

A "transcriptional regulatory polypeptide" refers to a protein or effector domain of protein that has the ability to modulate transcription. A transcriptional regulatory polypeptide may act as either a transcriptional activator, a transcriptional repressor, or in some rare cases, as either. Transcriptional regulatory polypeptides include, e.g., transcription factors and co-factors (e.g., KRAB, MAD, ERD, SID, nuclear factor kappa B subunit p65, early growth response factor 1, and nuclear hormone receptors, VP 16, VP64), endonucleases, integrases, recombinases, methyltransferases, histone acetyltransferases, histone deacetylases etc. Activators and repressors include co-activators and co-repressors.

The term "physiological conditions" refers to the salt concentration and ionic strength in an aqueous solution which characterize fluids found in human metabolism commonly referred to as physiological buffer or physiological saline. In general, these are represented by an intracellular pH of 7.1 and salt concentrations of 3-15 mM Na$^+$, 140 mM K$^+$, 6.3 mM Mg$^{+2}$, $10^{-4}$ mM Ca$^{+2}$, 3-15 mM Cl$^-$, and an extracellular pH of 7.4 and salt concentrations of 145 mM Na$^+$, 3 mM K$^+$, 1-2 mM Mg$^{+2}$, 1-2 mM Ca$^{+2}$, 110 mM Cl$^-$.

II. Aptamer-Guided Gene Targeting

The AGT described herein takes advantage of the fact that a single DNA molecule can have more than one function. By constructing a bifunctional DNA oligonucleotide to contain an aptamer region at its 5' end and a donor region to repair a genomic locus at its 3' end, it was possible to tether the donor DNA of choice to the site specific locus. In one embodiment the site specific locus is for endonuclease I-SceI. For example, by tethering the donor DNA to I-SceI, it was possible to deliver the donor DNA close to the site of the I-SceI DSB, and thus next to the desired targeting locus. Using bifunctional oligonucleotides in which the predicted hairpin structure of the aptamer to I-SceI formed, gene targeting was specifically induced when the I-SceI endonuclease was expressed and the I-SceI site was present in every genomic locus tested, in both yeast (up to 32-fold) and human cells (up to 16-fold). The data disclosed here show several lines of evidence that a DNA aptamer for a homing endonuclease, like I-SceI, can guide donor DNA to the vicinity of the nuclease cut site to increase the efficiency of gene correction close to the cut site and enhance the specificity of the genetic modification (FIG. 7). Exploiting the I-SceI aptamer in AGT, the donor molecule is brought in the vicinity of its target site, and this may not only increase HR with the desired locus but also potentially reduce the likelihood of random integration.

In addition to the efficacy of the I-SceI aptamer at increasing gene targeting, the AGT system provides a new function for aptamers. Aptamers themselves are a relatively new discovery, with the first aptamer selection protocols separately published in 1990. Aptamers have been used as biosensors and as therapeutics, but much of their function can be simplified to binding and fluorescing (sensor) or binding and inhibiting (therapy) or binding and being endocytosed (therapy). The aptamer for I-SceI disclosed herein binds and is targeted to a specific DNA site. This represents not only a new gene targeting strategy but also a new use of an aptamer. The work described here show that aptamers can be used as tools for gene targeting.

A. Aptamers

As discussed above, the bifunctional oligonucleotide includes an aptamer, preferably a DNA aptamer that binds to a DNA binding moiety. Nucleic acid aptamers are short single-stranded DNA or RNA oligos that are capable of binding a ligand (protein, small molecule, or even living cells) with high affinity due to their secondary structure. Most DNA or RNA is capable of forming a secondary structure, however only very rare sequences are capable of binding to a specific target with appreciable affinity. Aptamers, in addition to binding with high affinity, also bind with high specificity, as shown for an aptamer selected to bind theophylline. Aptamers are sometimes referred to as artificial antibodies, but aptamers have several advantages over antibodies, including ease and low cost of production which does not involve animals. Aptamers are less immunogenic than antibodies and are already being used as a therapeutic for humans.

Aptamers are obtained by rigorous selection, in which aptamers are "evolved" from pools of random DNA or RNA, leaving few (if any) sequences capable of binding the target out of a high number (usually 1014 or more) of starting sequences. The random library is typically flanked by fixed primer regions such that each oligo in the pool contains the sequence 5'-primer1-N20-60-primer2(reverse complement)-3', where N is a random base. The primers are used to amplify the library after selection by PCR. The process to generate aptamers by in vitro selection was developed by the Szostak and Gold groups independently in 1990 and the process has become known as systematic evolution of ligands by exponential enrichment (SELEX). The SELEX procedure involves the use of the random library of DNA/RNA sequences being incubated with the target, followed by a partitioning step to remove unbound sequences, then followed by an elution step to recover the binding sequences, and then an amplification step to generate a library of sequences enriched for binding. Over the years, several variants of SELEX have arisen. One variant of SELEX using capillary electrophoresis (CE) allows for SELEX to be performed in a much shorter amount of time due to much more efficient partitioning and the prevention of aptamers binding to the ligand support (the ligand flows freely in buffer). In as little as one round of selection, and almost always less than five, strong binding highly specific aptamers may be selected, as opposed to traditional SELEX which typically takes 10 or more rounds of selection.

CE-SELEX generated aptamers can have nM and even pM level disassociation constants.

B. DNA Binding Moieties

The DNA binding moiety bound by the bifunctional oligonucleotide is a molecule that specifically binds to DNA. The DNA can be nuclear or mitochondrial DNA. The molecule can be a protein, a complex of proteins, DNA, RNA, combinations of RNA and DNA. For example, the DNA binding moiety can be a site-specific homing endonucleases, zinc-finger nucleases (ZFNs), transcription activator-like effector nucleases (TALENs) or the Cas9 nuclease of the clustered regularly interspaced short palindromic repeat (CRISPR) system. Furthermore, the DNA moiety be any protein that facilitates the targeting process, such as transcription factors, HR proteins or even NHEJ proteins.

DNA binding proteins exist in all forms of life, but despite their prevalence there are only a handful of proteins evolved that are capable of binding to and cleaving double-stranded DNA in a site-specific manner. Those restriction endonucleases capable of achieving site-specific DNA DSBs are known as "homing" endonucleases, and they have high specificity due to a long recognition sequence (12-40 bp). Homing endonucleases have been studied since the late 1970s, and one of the first homing endonucleases studied was called "Omega" which later became known as I-SceI. The I-SceI endonuclease's natural function is to recognize a nonsymmetrical 18-bp sequence in yeast mitochondria of 5' TAG GGA TAA CAG GGT AAT 3' (SEQ ID NO: 1) on the intron-less allele and generate a DNA DSB at that location, propagating the intron containing allele and overwriting the previously intron-less allele through homologous recombination and gene conversion. Since its discovery, I-SceI has been used and continues to be used in almost every model system from bacteria to human cells to model DSB damage and repair.

The homing endonuclease can be LAGLIDADG (SEQ ID NO: 2) homing endonucleases, homing group I endonuclease families such as HNH and His-Cys box enzymes, HNH (I-HmuI), His-Cys box (I-PpoI) and GIY-YIG (I-TevI).

One embodiment provides genetically engineered homing endonuclease that is designed to bind and cut DNA at a specific nucleic acid sequence.

The disclosed compositions can localize to the nucleus by associating with a DNA-binding protein. DNA-binding proteins include transcription factors, polymerases, nucleases which cleave DNA molecules, and histones. DNA-binding proteins can have, for example, one or more HMG box, homeodomain, POU domain, zinc finger domains such as $C_2H_2$ and $C_2C_2$, amphipathic helix domains such as a leucine zipper, helix-loop-helix domain, and helix-turn-helix domains, or histone folds zinc fingers, that facilitate binding to nucleic acid. Other examples include transcription activator like effectors and replication proteins such as human replication protein A. The DNA-binding protein can be specific for a specific polynucleotide sequence, or preferably non-specifically binds to a polynucleotide. Alternatively, the DNA-binding protein can have more a combination of at least one polynucleotide binding domain that binds in a sequence specific manner and at least one polynucleotide binding-domain that binds DNA non-specifically.

1. HMG Domain

In some embodiments, the DNA-binding protein contains an HMG domain. Generally, the HMG domain includes a global fold of three helices stabilized in an 'L-shaped' configuration by two hydrophobic cores. The high mobility group chromosomal proteins HMG1 or HMG2, which are common to all eukaryotes, bind DNA in a non-sequence-specific fashion, for example to promote chromatin function and gene regulation. They can interact directly with nucleosomes and are believed to be modulators of chromatin structure. They are also important in activating a number of regulators of gene expression, including p53, Hox transcription factors and steroid hormone receptors, by increasing their affinity for DNA. HMG proteins include HMG-1/2, HMG-I(Y) and HMG-14/17.

The HMG-1/2-box proteins can be further distinguished into three subfamilies according to the number of HMG domains present in the protein, their specific of sequence recognition and their evolutionary relationship. The first group contains chromosomal proteins bound to DNA with no sequence specificity (class I, HMG1 and HMG2), the second contains ribosomal and mitochondrial transcription factors which show sequence specificity in the presence of another associating factor when bound with DNA (class II, yeast ARS binding protein ABF-2, UBF and mitochondrial transcription factor mtTF-1), and the third contains gene-specific transcription factors which show sequence specific DNA binding (class III, lymphoid enhancer-binding factors LEF-1 and TCF-1; the mammalian sex-determining factor SRY, and the closely related SOX proteins; and the fungal regulatory proteins Mat-MC, Mat-a1, Stel1 and Rox1). The HMG1/2-box DNA binding domain is about 75 to about 80 amino acids and contains highly conserved proline, aromatic and basic residues. Common properties of HMG domain proteins include interaction with the minor groove of the DNA helix, binding to irregular DNA structure, and the capacity to modulate DNA structure by bending.

SOX (SRY-type HMG box) proteins have critical functions in a number of developmental processes, including sex determination, skeleton formation, pre-B and T cell development and neural induction. SOX9 plays a direct role during chondrogenesis by binding and activating the chondrocyte-specific enhancer of the Col2a1 gene. Loss of SOX9 gene function leads to the genetic condition known as Campomelic Dysplsia (CD), a form of dwarfism characterized by extreme skeletal malformation, and one in which three-quarters of XY individual are either intersexes or exhibit male to female sex reversal. There are more than 20 members cloned in SOX family. All of which contain an HMG domain, which can bind specifically to the double strand DNA motif and shares >50% identify with the HMG domain of SRY, the human testis-determining factor. The preferred DNA-binding site of SOX9 have been defined to be AGAACAATGG (SEQ ID NO: 3), which contains the SOX core-binding element (SCBE), AACAAT, flanking 5'AG and 3'GG nucleotides enhance binding by SOX9.

In some embodiments, the DNA-binding protein has at least one HMG box domain, generally at least two, more particularly 2-5 HMG box domains. The HMG box domain can bind to an AT rich DNA sequence, for example, using a large surface on the concave face of the protein, to bind the minor groove of the DNA. This binding bends the DNA helix axis away from the site of contact. The first and second helices contact the DNA, their N-termini fitting into the minor groove whereas helix 3 is primarily exposed to solvent. Partial intercalation of aliphatic and aromatic residues in helix 2 occurs in the minor groove.

2. Helix-Turn-Helix

The DNA-binding proteins can have a helix-turn-helix motif or at least a polynucleotide binding region of a helix-turn-helix protein. Helix-turn-helix proteins have a similar structure to bacterial regulatory proteins such as the λ repressor and cro proteins, the lac repressor and so on which bind as dimers and their binding sites are palindromic. They contain 3 helical regions separated by short turns which is why they are called helix-turn-helix proteins. One protein helix (helix 3) in each subunit of the dimer occupies the major groove of two successive turns of the DNA helix. Thus, in another embodiment, the DNA-binding protein can form dimers or other multi-component complexes, and have 1 to 3 helices.

3. Homeodomain

In yet another embodiment, the DNA-binding protein includes a homeodomain or a portion of a homeodomain protein. Homeodomain proteins bind to a sequence of 180 base pairs initially identified in a group of genes called homeotic genes. Accordingly, the sequence was called the homeobox. The 180 bp corresponds to 60 amino acids in the corresponding protein. This protein domain is called the homeodomain. Homeodomain-containing proteins have since been identified in a wide range of organisms including vertebrates and plants. The homeodomain shows a high degree of sequence conservation. The homeodomain contains 4 α helical regions. Helices II and III are connected by 3 amino acids comprising a turn. This region has a very similar structure to helices II and III of bacterial DNA binding proteins.

4. Zinc Finger

The DNA-binding protein can have a zinc finger domain or at least a portion of a zinc finger protein. Zinc finger proteins have a domain with the general structure: Phe (sometimes Tyr)-Cys-2 to 4 amino acids-Cys-3 amino acids-Phe (sometimes Tyr)-5 amino acids-Leu-2 amino acids-His-3 amino acids-His. The phenylalanine or tyrosine residues which occur at invariant positions are required for DNA binding. Similar sequences have been found in a range of other DNA binding proteins though the number of fingers varies. For example, the SP 1 transcription factor which binds to the GC box found in the promoter proximal region of a number of genes has 3 fingers. This type of zinc finger which has 2 cysteines and 2 histidines is called a $C_2H_2$ zinc finger.

Another type of zinc finger which binds zinc between 2 pairs of cysteines has been found in a range of DNA binding proteins. The general structure of this type of zinc finger is: Cys-2 amino acids-Cys-13 amino acids-Cys-2 amino acids-Cys. This is called a $C_2C_2$ zinc finger. It is found in a group of proteins known as the steroid receptor superfamily, each of which has 2 $C_2C_2$ zinc fingers.

5. Leucine Zipper

The DNA-binding protein can have a leucine zipper or at least a portion of a leucine zipper protein. The first leucine zipper protein was identified from extracts of liver cells, and it was called C/EBP because it is an enhancer binding protein and it was originally thought to bind to the CAAT promoter proximal sequence. C/EBP will only bind to DNA as a dimer. The region of the protein where the two monomers join to make the dimer is called the dimerization domain. This lies towards the C-terminal end of the protein. When the amino acid sequence was examined it was found that a leucine residue occurs every seventh amino acid over a stretch of 35 amino acids. If this region were to form an a helix then all of these leucines would align on one face of the helix.

Because leucine has a hydrophobic side chain, one face of the helix is very hydrophobic. The opposite face has amino acids with charged side chains which are hydrophilic. The combination of hydrophobic and hydrophilic characteristics gives the molecule is amphipathic moniker. Adjacent to the leucine zipper region is a region of 20-30 amino acids which is rich in the basic (positively charged) amino acids lysine and arginine. This is the DNA binding domain—often referred to as the bZIP domain—the basic region of the leucine zipper. C/EBP is thought to bind to DNA by these bZIP regions wrapping round the DNA helix The leucine zipper—bZIP structure has been found in a range of other proteins including the products of the jun and fos oncogenes. Whereas C/EBP binds to DNA as a homodimer of identical subunits, fos cannot form homodimers at all and jun/jun homodimers tend to be unstable. However fos/jun heterodimers are much more stable. These fos/jun heterodimers correspond to a general transcription factor called AP1 which binds to a variety of promoters and enhancers and activates transcription. The consensus AP1 binding site is TGACTCA which is palindromic.

6. Helix-Loop-Helix

The DNA-binding protein can have a helix-loop-helix domain or a polynucleotide binding portion of a helix-loop-helix protein. Helix-loop-helix proteins are similar to leucine zippers in that they form dimers via amphipathic helices. They were first discovered as a class of proteins when a region of similarity was noticed between two enhancer binding proteins called E47 and E12. This conserved region has the potential to form two amphipathic separated by a loop hence helix-loop-helix. Next to the dimerization domain is a DNA binding domain, again rich in basic amino acids and referred to as the bHLH domain. These structures are also found in a number of genes required for development of the *Drosophila* nervous system—the Achaete-scute complex, and in a protein called MyoD which is required for mammalian muscle differentiation.

7. Histone Fold

The DNA-binding protein can be a histone polypeptide, a fragment of a histone polypeptide, or at least one histone fold. Histone folds exist in histone polypeptides monomers assembled into dimers. Histone polypeptides include H2A, H2B, H3, and H4 which can form heterodimers H2A-2B and H3-H4. It will be appreciated that histone-like polypeptides can also be used in the disclosed compositions and methods. Histone-like polypeptides include, but are not limited to, HMf or the histone from *Methanothermous fervidus*, other archaeal histones known in the art, and histone-fold containing polypeptides such as MJ1647, CBF, TAFII or transcription factor IID, SPT3, and Dr1-DRAP (Sanderman, K., et al., *Cell. Mol. Life Sci.* 54:1350-1364 (1998).

8. Mitochondrial Transcription Factors

The DNA-binding protein can be a mitochondrial transcription factor. It will be appreciated that in some embodiments, the disclosed compositions can localize to the mitochondria by associating with a mitochondrial DNA-binding protein, such as a mitochondrial transcription factor.

a. Transcription Factor A, Mitochondria (TFAM)

The DNA-binding protein can be TFAM. TFAM is a member of the high mobility group (HMG) of proteins having two HMG-box domains. An exemplary TFAM has GenBank Accession No. NM 003201. TFAM as well as other HMG proteins bind, wrap, bend, and unwind DNA. From N-terminus to C-terminus, mature TFAM includes four domains, a first HMG box (also referred to herein as HMG box 1), followed by a linker region (also referred to herein as linker), followed by a second HMG box (also referred to herein as HMG box 2), followed by a C-terminal tail. Functional fragments of TFAM can include, but are not limited to, a fragment of full-length TFAM sufficient to bind non-specifically to a polynucleotide, a fragment of full-length TFAM sufficient to bind specifically to the mtDNA light strand promoter (LSP), the mtDNA heavy strand promoter 1 (HSP1), the mtDNA heavy stand promoter 2 (HSP2), or combinations thereof, a fragment of full-length TFAM sufficient to induce mitochondrial transcription, a fragment of full-length TFAM sufficient to induce oxidative phosphorylation, a fragment of full-length TFAM sufficient to induce mitochondrial biogenesis, and combinations thereof.

b. Transcription Factor B1, Mitochondrial (TFB1M)

The DNA-binding protein can be transcription factor B1, mitochondrial (TFB1M). An exemplary TFB1M has GenBank Accession No. AF151833. TFB1 is part of the complex involved in mitochondrial transcription. The process of transcription initiation in mitochondria involves three types of proteins: the mitochondrial RNA polymerase (POLRMT), mitochondrial transcription factor A (TFAM), and mitochondrial transcription factors B1 and B2 (TFB1M, TFB2M). POLRMT, TFAM, and TFB1M or TFB2M assemble at the mitochondrial promoters and begin transcription. TFB1M has about 1/10 the transcriptional activity of TFB2M, and both TFBs are also related to rRNA methyltransferases and TFB1M can bind S-adenosylmethionine and methylate mitochondrial 12S rRNA. Additionally, TFB1M and TFB2M can bind single-stranded nucleic acids.

c. Transcription Factor B2, Mitochondrial (TFB2M)

The DNA-binding protein can be TFB2M. An exemplary TFB2M polypeptide has GenBank Accession No. AK026835. TFB2M also possesses a Rossmann-fold making it part of the NAD-binding protein family. TFB2M levels modulate mtDNA copy number and levels of mitochondrial transcripts as would be expected of a mitochondrial transcription factor.

d. Polymerase (RNA) Mitochondrial (DNA Directed) (POLRMT)

The DNA-binding protein can be POLRMT. An exemplary POLRMT polypeptide has GenBank Accession No. NM_005035. POLRMT is a mitochondrial RNA polymerase similar in structure to phage RNA polymerases. Unlike phage polymerases, POLRMT contains two pentatricopeptide repeat (PPR) domains involved in regulating mitochondrial transcripts. It is appreciated by those skilled in the art that deletion of regulatory domains enables constitutive function.

C. Donor DNA

The bifunctional oligonucleotides include donor DNA that is used to modify genetic material such as a defective gene. The donor DNA can be synthetic single-stranded DNA oligos that are short sequences of DNA typically 90 nt or less that are often used in genome editing. Oligos are used to modify a specific sequence in the genome by containing homology to the targeted sequence. The homology between the donor DNA and the target site can be 70% to 100%, typically 85% to 100%, even more typically 90% to 100%. Oligos can be chemically synthesized quickly and cheaply and can achieve efficient gene editing at a similar frequency to donors with longer homology lengths, including donor plasmids or PCR products (36). Gene correction by oligos can be obtained even with homology to the target locus as low as 30 nucleotides. The donor DNA is sufficiently complementary to hybrize to the target nucleic acid to hybridize with the target nucleic acid under physiological conditions.

If the composition includes a donor polynucleotide sequence that includes at least a segment with homology to the target DNA sequence, the methods can be used to add, i.e., insert or replace, nucleic acid material to a target DNA sequence (e.g., to "knock in" a nucleic acid that encodes for a protein, an siRNA, an miRNA, etc.), to add a tag, to add a regulatory sequence to a gene, to modify a nucleic acid sequence, etc. The compositions can be used to modify DNA in a site-specific, i.e., "targeted", way, for example gene knock-out, gene knock-in, gene editing, gene tagging, etc. as used in, for example, gene therapy, e.g., to treat a disease or as an antiviral, antipathogenic, or anticancer therapeutic.

In applications in which it is desirable to insert a polynucleotide sequence into a target DNA sequence, a polynucleotide including a donor sequence to be inserted is also provided to the cell. By a "donor sequence" or "donor polynucleotide" or "donor oligonucleotide" it is meant a nucleic acid sequence to be inserted at the cleavage site. The donor polynucleotide typically contains sufficient homology to a genomic sequence at the cleavage site, e.g., 70%, 80%, 85%, 90%, 95%, or 100% homology with the nucleotide sequences flanking the cleavage site, e.g., within about 50 bases or less of the cleavage site, e.g., within about 30 bases, within about 15 bases, within about 10 bases, within about 5 bases, or immediately flanking the cleavage site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) will support homology-directed repair. Donor sequences can be of any length, e.g., 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence includes a non-homologous sequence flanked by two regions of homology, such that homology-directed repair between the target DNA region and the two flanking sequences results in insertion of the non-homologous sequence at the target region.

Donor sequences can also include a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence can include certain sequence differences as compared to the genomic sequence, e.g., restriction sites, nucleotide polymorphisms, selectable markers (e.g., drug resistance genes, fluorescent proteins, enzymes etc.), etc., which can be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

The donor sequence can be a single-stranded DNA, single-stranded RNA, double-stranded DNA, or double-stranded RNA. It can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. Proc. Natl. Acad. Sci. USA 84:4959-4963 (1987); Nehls et al. Science 272:886-889 (1996). Additional methods for protecting exogenous polynucleotides from degradation include, but are not limited to, addition of terminal amino group(s) and the use of modified internucleotide linkages such as, for example, phosphorothioates, phosphor amidates, and O-methyl ribose or deoxyribose residues.

As an alternative to protecting the termini of a linear donor sequence, additional lengths of sequence can be included outside of the regions of homology that can be degraded without impacting recombination. A donor sequence can be introduced into a cell as part of a vector molecule having additional sequences such as, for example, replication origins, promoters and genes encoding antibiotic resistance.

III. Methods of Use

The disclosed bifunctional oligonucleotides can be used to modify genetic material in a subject, preferably a human subject. Genetic modification is typically referred to as gene therapy. Thus, the disclosed bifunctional oligonucleotides can be used to treat genetic disorders. Representative genetic disorders that can be treated include, but are not limited to Severe Combined Immune Deficiency (ADA-SCID), Chronic Granulomatus Disorder (CGD), Hemophilia, congenital blindness, lysosomal storage disease and muscular dystrophy, among others. Other diseases that can be treated include, but are not limited head and neck cancer, prostate cancer, pancreas cancer, and cancers in the brain, skin, liver, colon, breast and kidney.

Generally, the bifunctional oligonucleotides are designed to repair or replace a portion of the subject's genome. The bifunctional oligonucleotides are administered to the subject in an amount effective to modify the subject's genome. In certain embodiments, the DNA binding moiety is administered to the subject before, after, or concurrent with the bifunctional oligonucleotides.

IV. Formulations

Compositions and methods for increasing stability of nucleic acid half-life and nuclease resistance are known in the art, and can include one or more modifications or substitutions to the nucleobases, sugars, or linkages of the polynucleotide. For example, the bifunctional oligonulceotides can be custom synthesized to contain properties that are tailored to fit a desired use. Common modifications include, but are not limited to use of locked nucleic acids, unlocked nucleic acids (UNA's), morpholinos, peptide nucleic acids (PNA), phosphorothioate linkages, phosphonoacetate, linkages, propyne analogs, 2'-O-methyl RNA, 5-Me-dC, 2'-5' linked phosphodiester linkage, Chimeric Linkages (Mixed phosphorothioate and phosphodiester linkages and modifications), conjugation with lipid and peptides, and combinations thereof.

In some embodiment, the polynucleotide includes internucleotide linkage modifications such as phosphate analogs having achiral and uncharged intersubunit linkages (e.g., Sterchak, E. P. et al., Organic Chem., 52:4202, (1987)), or uncharged morpholino-based polymers having achiral intersubunit linkages (see, e.g., U.S. Pat. No. 5,034,506). Some internucleotide linkage analogs include morpholidate, acetal, and polyamide-linked heterocycles. Locked nucleic acids (LNA) are modified RNA nucleotides (see, for example, Braasch, et al., Chem. Biol., 8(1):1-7 (2001)). Commercial nucleic acid synthesizers and standard phosphoramidite chemistry are used to make LNAs. Other backbone and linkage modifications include, but are not limited to, phosphorothioates, peptide nucleic acids, tricyclo-DNA, decoy oligonucleotide, ribozymes, spiegelmers (containing L nucleic acids, an aptamer with high binding affinity), or CpG oligomers.

Phosphorothioates (or S-oligos) are a variant of normal DNA in which one of the nonbridging oxygens is replaced by a sulfur. The sulfurization of the internucleotide bond dramatically reduces the action of endo- and exonucleases including 5' to 3' and 3' to 5' DNA POL 1 exonuclease, nucleases S1 and P1, RNases, serum nucleases and snake venom phosphodiesterase. In addition, the potential for crossing the lipid bilayer increases. Because of these important improvements, phosphorothioates have found increasing application in cell regulation. Phosphorothioates are made by two principal routes: by the action of a solution of elemental sulfur in carbon disulfide on a hydrogen phosphonate, or by the more recent method of sulfurizing phosphite triesters with either tetraethylthiuram disulfide (TETD) or 3H-1, 2-bensodithiol-3-one 1,1-dioxide (BDTD).4 The latter methods avoid the problem of elemental sulfur's insolubility in most organic solvents and the toxicity of carbon disulfide. The TETD and BDTD methods also yield higher purity phosphorothioates. (See generally, Uhlmann and Peymann, 1990, Chemical Reviews 90, at pages 545-561 and references cited therein, Padmapriya and Agrawal, 1993, Bioorg. & Med. Chem. Lett. 3, 761).

Peptide nucleic acids (PNA) are molecules in which the phosphate backbone of oligonucleotides is replaced in its entirety by repeating N-(2-aminoethyl)-glycine units and phosphodiester bonds are replaced by peptide bonds. The various heterocyclic bases are linked to the backbone by methylene carbonyl bonds. PNAs maintain spacing of heterocyclic bases that is similar to oligonucleotides, but are achiral and neutrally charged molecules. Peptide nucleic acids are typically comprised of peptide nucleic acid monomers. The heterocyclic bases can be any of the standard bases (uracil, thymine, cytosine, adenine and guanine) or any of the modified heterocyclic bases described below. A PNA can also have one or more peptide or amino acid variations and modifications. Thus, the backbone constituents of PNAs may be peptide linkages, or alternatively, they may be non-peptide linkages. Examples include acetyl caps, amino spacers such as 8-amino-3,6-dioxaoctanoic acid (referred to herein as 0-linkers), and the like. Methods for the chemical assembly of PNAs are well known. See, for example, U.S. Pat. Nos. 5,539,082, 5,527,675, 5,623,049, 5,714,331, 5,736,336, 5,773,571 and 5,786,571. In some embodiments, the polynucleotide includes one or more chemically-modified heterocyclic bases including, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-D-ribofuranosyl)pyridine (2-aminopyridine), and various pyrrolo- and pyrazolopyrimidine derivatives, 4-acetylcytosine, 8-hydroxy-N-6-methyladenosine, aziridinylcytosine, 5-(carboxyhydroxylmethyl) uracil, 5-bromouracil, 5-carboxymethylaminomethyl-2-thiouracil, 5-carboxymethylaminomethyluracil, dihydrouracil, N6-isopentenyladenine, 1-methyladenine, 1-methylpseudouracil, 1-methyl guanine, 1-methylinosine, 2,2-dimethylguanine, 2-methyladenine, 2-methylguanine, 3-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, 2,6-diaminopurine, and 2'-modified analogs such as, but not limited to O-methyl, amino-, and fluoro-modified analogs. Inhibitory RNAs modified with 2'-flouro (2'-F) pyrimidines appear to have favorable properties in vitro (Chiu and Rana 2003; Harborth et al. 2003). Moreover, one report recently suggested 2'-F modified siRNAs have enhanced activity in cell culture as compared to 2'-OH containing siRNAs (Chiu and Rana 2003). 2'-F modified siRNAs are functional in mice but that they do not necessarily have enhanced intracellular activity over 2'-OH siRNAs.

In some embodiments the polynucleotide include one or more sugar moiety modifications, including, but are not limited to, 2'-O-aminoethoxy, 2'-O-amonioethyl (2'-OAE), 2'-O-methoxy, 2'-O-methyl, 2-guanidoethyl (2'-OGE), 2'-0,4'-C-methylene (LNA), 2'-O-(methoxyethyl) (2'-OME) and 2'-O—(N-(methyl)acetamido) (2'-OMA).

EXAMPLES

Materials and Methods
Aptamer Selection

The protein of interest, I-SceI, was provided by F. Gimble (Purdue University, West Lafayette, Ind.) in storage buffer (10 mM $KPO_4$, pH 7.4, 100 nM EDTA, 1 mM DTT, 100 mM NaCl and 50% glycerol). Before selection, to remove storage buffer components, I-SceI was dialyzed in run buffer 1 (RB1), 50 mM Tris-HCl at pH 8.2, yielding a concentration of 3 mM I-SceI in RB1. RB1 was the run buffer used for the capillary electrophoresis. The DNA library was purchased from Alpha DNA (Montreal, Quebec, Canada) and contained the following sequence: 5'_CTTCTGCCCGCCTC-CTTCC-(N)36-GAC GAGATAGGCGGACACT_3' (SEQ ID NO: 4) (Table 1). The library was composed of a sequence with 36 random nucleotides flanked by two fixed 19-base regions used later as primer sequences for polymerase chain reaction (PCR) amplification using the forward aptamer amplifying primer P1 (5'_CTTCTGCCCGCCTC CTTCC_3' (SEQ ID NO: 5)) and the reverse primer P2 (5'_AGTGTCCGCCTATCTCGTC_3' (SEQ ID NO: 6)) (Table 1).

Figures 9A, 9B, 9C, 9D:
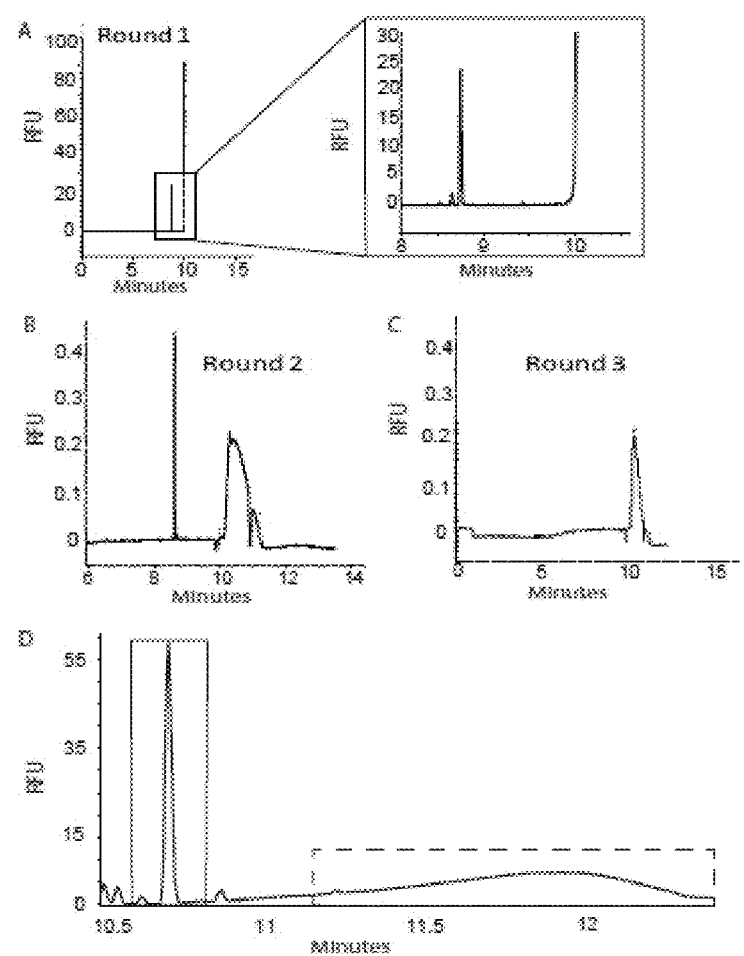

The protocol for SELEX using capillary electrophoresis (CE) was essentially as described earlier (Berezovski, et al., Nat. Protoc., 1:1359-1369 (2006)), but with a few modifications. Initial calibrations were done with a serial dilution of the aptamer library in RB1. The free DNA run time with 100 nM of the library was determined (FIG. 8A). The initial bulk affinity assay was performed with 1.5 mM I-SceI and 100 nM DNA to visualize peaks corresponding to I-SceI-DNA complexes and determine the aptamer collection window from the beginning of the first complex peak to the end of the last complex peak (FIG. 8B). CE was done using a Beckman Coulter (Atlanta, Ga., USA) P/ACE MDQ with laser-induced fluorescence (LIF) detection. The LIF was composed of a 488-nm air-cooled argon ion laser along with an on-board detector. CE runs were carried out with a voltage of 10 kV. The first round of selection began after determination of the collection window based on the bulk affinity analysis. For the initial round of in vitro selection, the DNA library (5 µl at 200 µM) was mixed with 5 µl of selection buffer 3 (SB3) (100 mM Tris-HCl at pH 8.2, 200 mM NaCl and 10 mM $MgCl_2$) for a final concentration of 100 µM DNA library, 50 mM Tris-HCl at pH 8.2, 100 mM NaCl and 5 mM $MgCl_2$. This mixture was heated in the BioRad iCycler™ to 94° C. for 1 min, and then cooled to 20° C. at a rate of 0.5° C./s. After the folding of the DNA library, 5 µl of 200 nM I-SceI dissolved in selection buffer 1 (SB1) (50 mM Tris-HCl at pH 8.2, 100 mM NaCl and 5 mM $MgCl_2$) was added to 5 µl of the DNA-SB3 mixture to make the final volume to 10 µl. This brought the final concentrations to 50 µM DNA library, 100 nM I-SceI, 100 mM NaCl, 5 mM $MgCl_2$ and 50 mM Tris-HCl (pH 8.2). The collection window was from the beginning of the first complex peak to the end of the last complex peak, well before the free DNA peak. The fraction collected was typically 0.3-0.5 m 1 that was collected into a tube containing 10 µl of the above mixture except without any additional DNA. After 15 min of incubation at room temperature, this new mixture was used in subsequent rounds of selection. Despite the reduction in I-SceI concentration compared with the bulk affinity assay, complexes were still observed for the first round of selection (FIG. 9A). In the second round of selection, the ratio of DNA forming a complex compared with free DNA was much higher than in the first round (FIG. 9B). Selection proceeded to a third round; however, no complexes were observed due to the low amount of total DNA (FIG. 9C). The fraction collected from the second round of CE containing DNA forming a complex with I-SceI was used for subsequent analysis as an aptamer pool.

Quantitative Real-Time-PCR and Amplification of the Aptamer Pool

After the aptamer selection, the collected fraction containing the aptamer pool was analysed through quantitative real-time PCR (qRT-PCR) using the ABI (Carlsbad, Calif., USA) StepOnePlus Real-Time PCR system. qRT-PCR analysis was essential to determine the optimum number of cycles for subsequent PCR amplification of the aptamer pool. qRT-PCR was done with the forward aptamer-amplifying primer P1 (5'_CTTCTGCCCGCCTCCTTCC_3' (SEQ ID NO: 5)) and the reverse primer P2 (5'_AGTGTCCGC-CTATCTCGTC_3' (SEQ ID NO: 6)), respectively (Table 1). The primers were designed using OligoAnalyzer (http://www.idtdna.com/analyzer/Applications/OligoAnalyzer/) to limit complementarity to each other, thus to reduce occurrence of primer dimers during PCR amplification reactions, and were ordered from Eurofins MWG Operon (Huntsville, Ala., USA). For amplification, 20 µl of PCR mix was prepared consisting of 10 µl of 2× Quanta SYBR Green PCR Master Mix (Roche, Basel, Switzerland), 0.6 µl of 10 µM P1, 0.6 µl of 10 µM P2, 1 µl of collected fraction as template and 7.8 µl $H_2O$. The qRT-PCR set-up included one cycle with a denaturation step at 94° C. for 30 s, followed by 50 cycles with a denaturation step at 94° C. for 10 s, an annealing step at 55° C. for 10 s and an extension step at 72° C. for 10 s, followed by another extension at 72° C. for 1 min, ending by holding at 4° C.

Following qRT-PCR, the fraction containing the potential aptamers was amplified using standard PCR. PCR was done in a 100 m 1 volume consisting of 1 m 1 of 5U/µl Ex Taq polymerase, 3 µl of 10 µM forward primer P1, 3 µl of 10 µM reverse primer P2, 10 µl of 10× $Mg^{2+}$ buffer (Takara Ex Taq, Clontech Laboratories, Mountainview, Calif., USA), 8 µl of 2.5 mM each dNTP, 70 µl $H_2O$ and 5 µl of the collected fraction from capillary electrophoresis. In a previous protocol to select DNA aptamers, it was shown that over-amplification of the random oligonucleotide library leads to formation of non-specific products (Berezovski, et al., *Anal. Chem.*, 77:1526-1529 (2005)); therefore, the random library was only amplified to about 50% of the maximum yield as measured by qRT-PCR.

Cloning and Sequencing

Post-selection DNA cloning of the aptamer pool was done with the TOPO Zero Blunt Cloning Kit (Invitrogen, Grand Island, N.Y., USA). Standard PCR with unlabeled primers P1 and P2 was used to generate double-stranded DNA containing the aptamer sequence, which was then blunt-end ligated into the PCR-Blunt II-TOPO vector that contains the kanamycin resistance gene. After transformation into *Escherichia coli* DH5a cells, colonies were selected for growth on kanamycin-containing media (kanamycin final concentration was 40 μg/ml). Plasmid DNA was crudely extracted by placing selected colonies into 50 ml of RNase/DNase-free water and incubating in a boiling water bath for 5 min. Debris was pelleted by centrifugation for 10 min at 10 000 g and the supernatant was used for an asymmetric PCR. Asymmetric PCR, in which the concentration of the P1 primer was 10-fold higher (10 μM) than that of the P2 primer (1 μM), with FAM labelled primer P1 (P1-FAM) and unlabeled primer P2 were used on the plasmid DNA to predominately generate the strand of interest, which was then analyzed using CE with LIF. PCR products were used with 1.5 μM I-SceI in the same manner described previously for CE analysis. Individual plasmids that showed strong binding through their asymmetric PCR products were isolated using the GeneJET Plasmid Miniprep Kit (Thermo Scientific, Pittsburgh, Pa., USA) and sequenced by Eurofins MWG Operon (Huntsville, Ala., USA). Based on sequencing results, several candidate aptamers were chosen and ordered as salt-free oligonucleotides. Consensus sequence was analyzed using ClustalW2.

Electrophoretic Mobility Shift Assay

Potential aptamer oligonucleotides and a negative control oligonucleotide were 50 labelled with P32 g-ATP using T4 Polynucleotide Kinase (New England Biolabs, Ipswich, Mass., USA). The negative control (P1-r-P2) consisted of an oligonucleotide of the same length as the random DNA library (74 bases), contained the same flanking primer regions and had a fixed sequence for its internal region 5'-CTTCTGCCCGCCTCCTTCCGGTCGGGCACACCT-GTCATACCCAATCTCGAG GCCAGACGAGATA GGCGGACACT-3' (SEQ ID NO: 7) (Table 1). The internal region was chosen using a random DNA sequence generator with a specified GC content of 50% (http://www.faculty.ucr.edu/_mmaduro/random.htm). Electrophoretic mobility shift assay (EMSA) conditions were as described previously (Ruff, et al., *ISRN Mol. Biol.*, Article ID 939083, doi: 10.5402/2012/939083, 9 pages (2012)), with some modifications. For a more detailed description see Yeast Strains Three different strain backgrounds were used for these studies, BY4742 (MATa his3Δ1 leu2Δ0 lys2Δ0 ura3Δ0) (Storici, et al., *Proc. Natl Acad. Sci. USA*, 100:14994-14999 (2003)), 55R5-3C [MATa ura1 omega⁻ C321 (chloramphenicol resistant)] (Dujon, B., *Cell.*, 20:185-197 (1980)) and FRO-767 (leu2::HOcs[1], mataΔ::hisG, hoΔ, hmlΔ::ADE1, hmrΔ::ADE1, ade1, leu2-3,112, lys5, trp1::hisG, ura3-52, ade3::GAL::HO) (Storici, et al., *Nature*, 447:338-341 (2007)) (Table 2). The TRP5, ADE2 and LEU2 loci were tested in the BY4742 background. The TRP1, ADE2 and LEU2 loci were tested in the 55R5-3C background. The TRP5 locus was also tested in the FRO-767 background.

Figure 1:
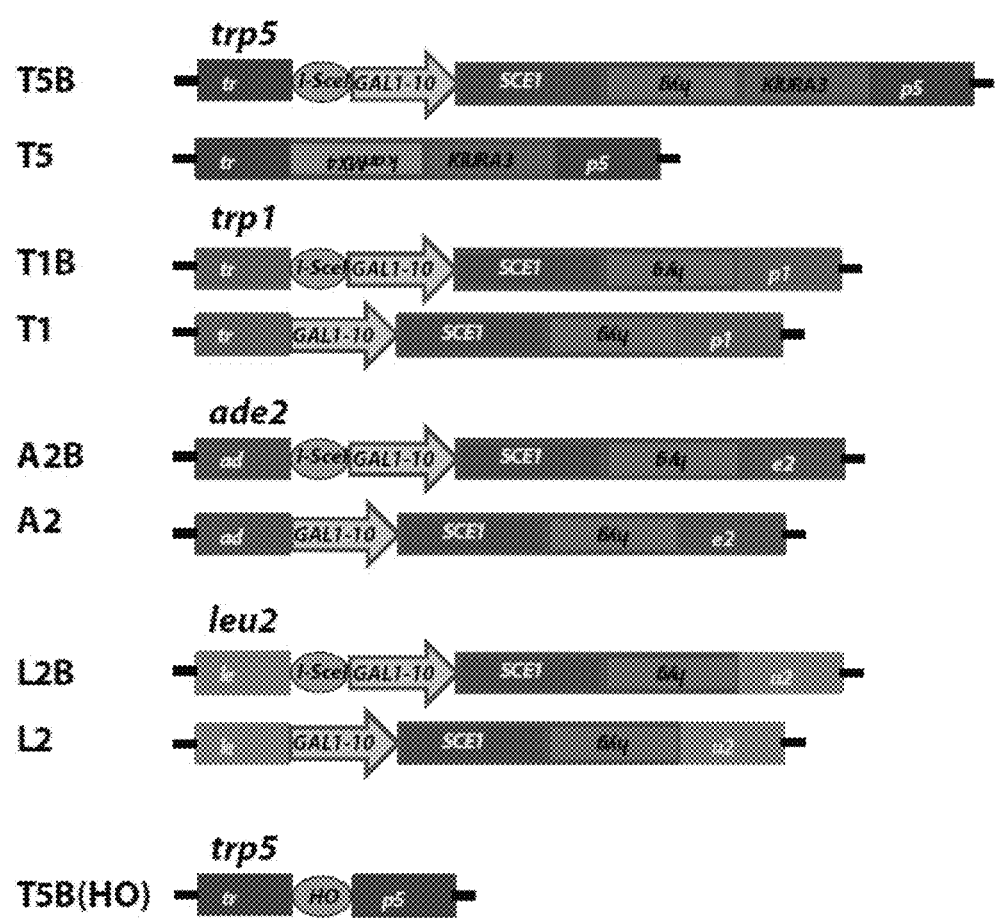
FIG. 1 shows a scheme of targeted yeast loci. The FRO-155/156 strain, shown above as T5B, contains the I-SceI break site (ellipse), and a cassette with the I-SceI gene SCE1 under the galactose inducible GAL1-10 promoter, the hygromycin resistance gene hyg, as well as the counterselectable KlURA3 gene in a construct that has been inserted into the TRP5 gene. FRO-526/527, shown as T5, contains only the kanMX4 gene and the KlURA3 gene in a cassette that has been inserted into the TRP5 gene. All other I-SceI strains shown contain the GSH cassette (the I-SceI gene SCE1 under the galactose inducible GAL1-10 promoter and the hyg gene) either with the I-SceI break site (T1B, A2B, L2B) shown as an ellipse or without the I-SceI site (T1, A2, and L2). Strain HK-225/226, shown as T5B(HO), contains the HO break site inserted into the TRP5 gene.

For the TRP5 locus, yeast strains FRO-155 (T5B) and FRO-526 (T5) (Storici, et al., *Proc. Natl Acad. Sci. USA*, 100:14994-14999 (2003)) were used (FIG. 1). Yeast haploid strain FRO-155 (MATa his3Δ1 leu2Δ0 lys2Δ0 trp5::GSHU lys2::Alu IR) contains the GSHU cassette (including the I-SceI gene SCE1 under the inducible GAL1-10 promoter, the hygromycin resistance gene hyg and the counterselectable URA3 gene from *Kluyveromyces lactis* (KlURA3 marker gene) and the I-SceI site (HOT site) in TRP5 (Storici, et al., *Proc. Natl Acad. Sci. USA*, 100:14994-14999 (2003)). FRO-526 is identical to FRO-155 except that instead of the GSHU cassette, the TRP5 gene is disrupted with the CORE-UK cassette (the counterselectable KlURA3 marker gene along with the KanMX4 gene conferring G418 resistance). These strains, along with isogenic isolates FRO-156 (isogenic to FRO-155), and FRO-527 (isogenic to FRO-526) were used for gene correction at the TRP5 locus. Additionally, RAD52 deletion in FRO-155 was achieved by replacing the RAD52 gene with the kanMX4 gene in strains PAT-44 and PAT-45.

All other strains expressing I-SceI were generated by integrating the GSH cassette (including the I-SceI gene SCE1 under the inducible GAL1-10 promoter and the hygromycin resistance gene hyg) into each respective locus and strain background. For the strains to contain the I-SceI recognition site [T1B in which GSH with the I-SceI site was integrated into TRP1 (PAT-18, 19), A2B in which GSH with the I-SceI site was integrated into ADE2 (PAT-22, 23, 32, 33) and L2B in which GSH with the I-SceI site was integrated into LEU2 (BPL-1, 2, PAT-20, 21, 34-37)], the GSH cassette was PCR-amplified from plasmid pGSHU (Storici, et al., *Proc. Natl Acad. Sci. USA*, 100:14994-14999 (2003)) using primers with 50-base homology tails to the respective integration site along with the 18-base I-SceI site upstream of the GAL1-10 promoter (FIG. 1). The strains lacking the I-SceI site [T1 in which GSH without the I-SceI site was integrated into TRP1 (PAT-24, 25), A2 in which GSH without the I-SceI site was integrated into ADE2 (PAT-28, 29, 42, 43) and L2 in which GSH without the I-SceI site was integrated into LEU2 (BPL-4, 5, PAT-26, 27, 38-41)] were generated in the same way except with primers lacking the I-SceI site (FIG. 1).

Strains HK-225 and HK-226 (isogenic to each other) derive from FRO-767 and were constructed as follows. First, the HO site in leu2 was eliminated by replacing leu2::HOcs with an insertion (Table 2). Second, a functional TRP1 gene was introduced in place of HIS3, and using the delitto perfetto approach (Stuckey, et al., *Methods Mol. Biol.*, 745:173-191 (2011)), the HO cut site (124 bp) was inserted in the middle of TRP5 exactly in the same position in which we had inserted the I-SceI site in the above described constructs. The sequence of the HO cut site was verified by sequence analysis.

A detailed list of the strains is presented in Table 2.

Yeast Transformations Using Oligonucleotides

Transformations were done as previously described with minor variations (Stuckey, et al., *Methods Mol. Biol.*, 745: 173-191 (2011)). Briefly, 50 ml of yeast extract-peptone-lactic acid (YPLac) (lactic acid 2%), pH 5.8, or yeast extract-peptone-dextrose (YPD) liquid culture was inoculated about 24 h before transformation and incubated with vigorous shaking at 30° C. YPLac was used as a neutral carbon source so as not to induce I-SceI expression until plating the transformations to selective galactose-containing media. YPD was used to repress I-SceI expression until plating the transformations to selective glucose-containing media. Transformations were done with 1 nmol of total oligonucleotide DNA, with the exception of the PAGE-purified oligonucleotides in which transformations were done with 500 pmol of total oligonucleotide DNA. For the transformations testing to determine whether the aptamer was working in trans, two oligonucleotides were used, 500 pmol of each oligonucleotide, such that the combined total oligonucleotide DNA used was 1 nmol. Sequences of oligonucleotides used for repair can be found in Table 1. Cells from each transformation were diluted appropriately and plated to synthetic complete medium lacking the respective amino acid and containing 2% galactose for I-SceI induction, 2 or 0.2% galactose for HO induction or 2% glucose for I-SceI or HO repression. The exception to this is the experiment to determine the position of the aptamer in the targeting DNA sequence (at the 5' or 3' end). For this experiment, I-SceI was induced 3 h by addition of galactose (final concentration 2%) to the liquid YPLac medium before transformation by oligonucleotides, and cells were plated on selective media containing glucose. Viability after transformation was calculated by plating to glucose-containing synthetic complete medium. Viability after transformation for the I-SceI-containing strains was typically 20-40% both on glucose and galactose. The HO-containing strain had a low viability after HO DSB induction, 0.53% in 2% galactose and 1.09% in 0.2% galactose, whereas its viability was about 25% in glucose. The frequency of gene correction is based on the number of transformants relative to $10^7$ viable cells that formed a colony on galactose-containing synthetic complete medium (or glucose-containing synthetic complete medium depending on the transformation experiment). Yeast cell culture and standard molecular biology techniques were used as previously described Human Cell Lines, Plasmids and Procedures Human embryonic kidney (HEK-293) cells were grown in Dulbecco's modified Eagle's medium (DMEM) (Mediatech, Manassas, Va., USA), supplemented with 10% heat-inactivated fetal bovine serum (Gemini Bio-Products, West Sacramento, Calif., USA) and 1× penicillin/streptomycin (Lonza, Walkersville, Md., USA). Cells were grown at 37° C. in a water-jacketed 5% $CO_2$ humidified incubator (Nu-Aire, Plymouth, Minn., USA). Plasmid pLDSLm contains the DsRed2 gene, responsible for producing red fluorescent protein (RFP), disrupted by a 37-bp region containing the 18-bp site for the I-SceI endonuclease preceded by two stop codons. Plasmid pEGFP300-disDsRed2 was modified to make plasmid pLDSLm. pEGFP300-disDsRed2 is identical to pdisEGFP300-disDsRed2 described in Katz et al. (Katz, et al., *PloS One*, in press (2014)) with the disrupted non-functional GFP replaced by a functional GFP gene. Although not relevant for this work, plasmid pEGFP300-disDsRed2 also contains a LexA DNA binding domain (DBD) site upstream of the CMV promoter of the disrupted DsRed2 gene (inserted using primers LexAF ACAGTGCTAAGTG-GATCCGTACTGTATGTACATACAGTACACCGTAT-TACCGC CATGCAT (SEQ ID NO: 8) and LexAR ATT-GAGTTCCTAGGATCCGTACTGTATGTACATACAGT-ACATCTCGGTCTATT CTTTTGA (SEQ ID NO: 9)) and a mutated LexA DBD site downstream of the disrupted DsRed2 gene's polyA tail (inserted using primers IVML-exAM-F CAAAAGAATAGACCGAGATGTACTGTA-CATATGTACAGTACGGATCTGGTAC CTTGTATTA (SEQ ID NO: 10) and IVMLexAM-R TAATACAAGGTAC-CAGATCCGTACTGTACATATGTACAGTACATC TCG-GTCTATTCTTTTG (SEQ ID NO: 11)). Plasmid pSce (a gift from M. Porteus, Stanford University, Calif., USA) contains the I-SceI endonuclease gene expressed under the CMV/CBA promoter as described previously (Porteus, M. H., *Science*, 300:763 (2003)). Cells were transfected using polyethylenimine (PEI, Polysciences, Warrington, Pa., USA) transfection reagent in 24-well plates seeded at a density of about 150 000 cells per well (Hirsch, et al., *PloS One*, 4:e7705 (2009); Grieger, et al., *Nat. Protocols*, 1:1412-1428 (2006)) 24 h before transfection. For transfections in HEK-293 cells, the plasmid DNA was used in the amount of 0.5 μg for the expression vector, as well as 0.5 μg for the targeted vector, and the repairing DNA oligonucleotide used was 1 μg, unless otherwise indicated. For the transfections with I-SceI digested pLDSLm, 0.5 m g of the linearized pLDSLm vector was used with 1 m g of repairing DNA oligonucleotide. Digestion of the pLDSLm vector was done using I-SceI (New England Biolabs, Ipswich, Mass., USA). Ten micrograms of plasmid pLDSLm was digested using 15 U I-SceI, 250 ng bovine serum albumin (BSA), 10×I-SceI buffer (New England Biolabs, Ipswich, Mass., USA) and water to a final volume of 50 μl. Digestions were done overnight at 37° C. In all transfection experiments, the oligonucleotides and the plasmid were diluted in DMEM without supplements, and then PEI was added, the solution was vortexed and added to the wells 10-15 min later. Red fluorescent cells were visualized by fluorescent microscopy using a Zeiss Observer A1 microscope and an AxioCam MRm camera (Zeiss, Thornwood, N.Y., USA). Frequencies of RFP positive cells were obtained by flow cytometric analysis using the BD FACS Aria II Cell Sorter (BD Biosciences, Sparks, Md., USA) for RFP detection 5-8 days following transfection. For certain transfections, wells of 24-well plates were seeded with 150,000 cells (on the day before transfection) and 5-8 days after transfection individual fluorescent cells per well were counted using a fluorescence microscope just before flow cytometry analysis. From the seeding time and the time of counting or flowcytometric analysis, cells are 8-10 times more numerous per well. Sequences of oligonucleotides used to repair the DsRed2 gene are listed in Table 1.

Mfold Secondary Structure Prediction

Secondary structure prediction software was used on the A7 aptamer-containing oligonucleotides used for gene correction. The program mfold was used to identify secondary structure at approximately physiological ion concentrations that were also used for the aptamer selection (90 mM $Na^+$ and 5 mM $Mg^{+2}$). Folding was done at either 30° C. (for the yeast oligonucleotides) or 37° C. (for the human oligonucleotides) (Romani, et al., *Front. Biosci.*, 5:D720-D734 (2000); Noda, et al., *Chem. Senses*, 30:i44-i45 (2005)).

Electrophoretic Mobility Shift Assay (EMSA)

Potential aptamer oligonucleotides and a negative control oligonucleotide were 5' labeled with $P^{32}$ γ-ATP using T4 Polynucleotide Kinase (New England Biolabs, Ipswich, Mass.). The negative control (P1-r-P2) consisted of an oligonucleotide of the same length as the random DNA library (74 bases), contained the same flanking primer regions, and had a fixed sequence for its internal region 5'-CTTCTGCCCGCCTCCTTCCGGTCGGGCACACCT-GTCATACCC AATCTCGAGGCCAGACGAGATAG-GCGGACACT-3' (SEQ ID NO: 7) (Table 1). The internal region was chosen using a random DNA sequence generator with a specified GC content of 50% (http://www.faculty.u-cr.edu/~mmaduro/random.htm). I-SceI was dialyzed before running the EMSA gels in Run Buffer 1 (RB1), 50 mM Tris-HCl at pH 8.2, as previously described. Bovine serum albumin (BSA) was purchased as a lyophilized powder through Sigma-Aldrich (St. Louis, Mo.) and was greater than 98% pure. BSA stock of 10 mg/ml was made in RB1 buffer.

The buffer conditions used for binding had several components described previously (22). Each reaction consisted of 2 μL 5×EMSA buffer 1 (100 mM Tris-HCl at pH 8.5, 250 mM NaCl, 10 μM ZnCl$_2$, 10 mM MgCl$_2$, 10% glycerol), 1 μL BSA (10 mg/ml), 1 μL freshly prepared 20 mM DTT, and 1 μL 100 mM MgCl$_2$ for a final buffer concentration of 20 mM Tris-HCl, 50 mM NaCl, 2 μM ZnCl$_2$, 22 mM MgCl$_2$, 1 mg/ml BSA, 24 mM DTT, and 2% glycerol. After mixing these components together, 2 μL of dialyzed I-SceI (total of 3 μM) for each reaction was added, bringing the volume to 7 pt. The radiolabeling of the oligonucleotides had varying efficiencies such that the counts per minute (cpm) measurement of the radioactivity for each labeled oligonucleotide was different. Reactions were aliquoted and 0.3 to 0.5 μl (20,000 cpm equivalent) of γP$^{32}$-labeled oligonucleotides were added. The reaction mixture of DNA and I-SceI was incubated for 70 minutes at room temperature. After incubation 2 μl of EMSA buffer 2 (120 mM Tris-HCl at pH 8, 600 mM NH$_4$Cl, 300 mM NaCl, 300 mM KCl, 30% glycerol, 0.25% bromophenol blue) was added. After addition of EMSA buffer 2 the samples were iced until loaded. The reactions were run on 4% polyacrylamide gels under non-denaturing conditions. Mini-gels were made with stock solutions of 40% acrylamide/bis-acrylamide (29:1), 1×Tris-borate EDTA (TBE), 10% ammonium persulfate (APS), and tetramethylethylenediamine (TEMED). Gels were run using the Mini-PROTEAN Tetra Cell apparatus from BioRad (Hercules, Calif.). Pre-run was done in 1×TBE buffer for 1 hour prior to loading of the samples. The samples were run in cold running buffer at 150 V until the bromophenol blue dye reached the bottom of the gel. The radioactivity in the gel was analyzed by Phosphor Imager (Molecular Dynamics—Typhoon Trio Imager™, GE Healthcare Life Sciences, Pittsburgh, Pa.). The imager was set to highlight saturated pixels. Due to the single-stranded DNA used, aggregates likely formed that were unable to enter the gel and these aggregates were reduced in the presence of protein.

TABLE 1

| (Supplementary Table 1) Oligonucleotides used in this study | | | |
|---|---|---|---|
| Name | SEQ ID NO: | Size | Sequence |
| Selection Oligos | | | |
| Library | 4 | 74 | 5' FAM-CTTCTGCCCGCCTCCTTCCNNNNNNNNNNNNNNNNNNNNNNNN NNNNNNNNNNNNNGACGAGATAGGCGGACACT 3' |
| P1 | 5 | 19 | 5' CTTCTGCCCGCCTCCTTCC 3' |
| P2 | 6 | 19 | 5' AGTGTCCGCCTATCTCGTC 3' |
| P1-FAM | 5 | 19 | 5' FAM-CTTCTGCCCGCCTCCTTCC 3' |
| P1-r-P2 | 7 | 74 | 5' CTTCTGCCCGCCTCCTTCCGGTCGGGCACACCTGTCATACCCA ATCTCGAGG CCAGACGAGATAGGCGGACACT 3' |
| Yeast Oligos | | | |
| P1-A7-P2.TRP5.40 | 12 | 114 | 5' CTTCTGCCCGCCTCCTTCC GCGGGCGCTGTTGACAGCGGTCAGGTGGATGGGATG GACGAGATAGGCGGACACTGGTTTTGATGAAGCTGTCGCGGAT CCCACATTCTGGGAAG 3' |
| TRP5.40.P1-A7-P2 | 13 | 114 | 5' GGTTTTGATGAAGCTGTCGCGGATCCCACATTCTGGGAA GCTTCTGCCCGCCT CCTTCC GCGGGCGCTGTTGACAGCGGTCAGGTGGATGGGATGGAC GAGATAGGC GGACACT 3' |
| P1-r-P2.TRP5.40 | 14 | 114 | 5' CTTCTGCCCGCCTCCTTCCGGTCGGGCACACCTGTCATACCC AATCTCGAGG CCAGACGAGATAGGCGGACACTGGTTTTGATGAAGCTGTCGCG GATCCCACATTCTG GGAAG 3' |
| A7.TRP5.54 | 15 | 90 | 5' GCGGGCGCTGTTGACAGCGGTCAGGTGGATGGGATG GGAAAAGGGTTTTGATGAA GCTGTCGCGGATCCCACATTCTGGGAAGACTTCAA 3' |
| A7.TRP5.54-P | 15 | 90 | 5' GCGGGCGCTGTTGACAGCGGTCAGGTGGATGGGATG GGAAAAGGGTTTTGATGAA GCTGTCGCGGATCCCACATTCTGGGAAGACTTCAA 3' |
| A7.TRP5.40 | 16 | 76 | 5' GCGGGCGCTGTTGACAGCGGTCAGGTGGATGGGATG GGTTTTGATGAAGCTGTCG CGGATCCCACATTCTGGGAAG 3' |

TABLE 1-continued (Supplementary Table 1) Oligonucleotides used in this study

| Name | SEQ ID NO: | Size | Sequence |
|---|---|---|---|
| A7.TRP5.40-P | 16 | 76 | 5' GCGGGCGCTGTTGACAGCGGTCAGGTGGATGGGATGGGTTTTGATGAAGCTGTCGCGGATCCCACATTCTGGGAAG 3' |
| A7.TRP1.54 | 17 | 90 | 5' GCGGGCGCTGTTGACAGCGGTCAGGTGGATGGGATGGTGGCAAGAATACCAAGAGTTCCTCGGTTTGCCAGTTATTAAAAGACTCGTATT 3' |
| A7.ADE2.54 | 18 | 90 | 5' GCGGGCGCTGTTGACAGCGGTCAGGTGGATGGGATGGGACATTATACCATTGATGCTTGCGTCACTTCTCAATTTGAAGCTCATTTGAGA 3' |
| A7.ADE2.40 | 19 | 76 | 5' GCGGGCGCTGTTGACAGCGGTCAGGTGGATGGGATGATACCATTGATGCTTGCGTCACTTCTCAATTTGAAGCTCA 3' |
| A7.LEU2.54 | 20 | 90 | 5' GCGGGCGCTGTTGACAGCGGTCAGGTGGATGGGATGCGCTTTCATGGCCCTACAACATGAGCCACCATTGCCTATTTGGTCCTTGGATAA 3' |
| A7.LEU2.40 | 21 | 76 | 5' GCGGGCGCTGTTGACAGCGGTCAGGTGGATGGGATGATGGCCCTACAACATGAGCCACCATTGCCTATTTGGTCCT 3' |
| C.TRP5.54 | 22 | 90 | 5' TTCTGCCCGCCTCCTTCCGACGAGATAGGCGGACACGGAAAAGGGTTTTGATGAAGCTGTCGCGGATCCCACATTCTGGGAAGACTTCAA 3' |
| C.TRP5.54-P | 22 | 90 | 5' TTCTGCCCGCCTCCTTCCGACGAGATAGGCGGACACGGAAAAGGGTTTTGATGAAGCTGTCGCGGATCCCACATTCTGGGAAGACTTCAA 3' |
| C.TRP5.40 | 23 | 76 | 5' TTCTGCCCGCCTCCTTCCGACGAGATAGGCGGACACGGTTTTGATGAAGCTCGCGGATCCCACATTCTGGGAAG 3' |
| C.TRP5.40-P | 23 | 76 | 5' TTCTGCCCGCCTCCTTCCGACGAGATAGGCGGACACGGTTTTGATGAAGCTGTCGCGGATCCCACATTCTGGGAAG 3' |
| C.TRP1.54 | 24 | 90 | 5' TTCTGCCCGCCTCCTTCCGACGAGATAGGCGGACACGTGGCAAGAATACCAAGAGTTCCTCGGTTTGCCAGTTATTAAAGACTCGTATT 3' |
| C.ADE2.54 | 25 | 90 | 5' TTCTGCCCGCCTCCTTCCGACGAGATAGGCGGACACCGCTTTCATGGCCCTACAACATGAGCCACCATTGCCTATTTGGTCCTTGGATAA 3' |
| C.ADE2.40 | 26 | 76 | 5' TTCTGCCCGCCTCCTTCCGACGAGATAGGCGGACACATGGCCCTACAACATGAGCCACCATTGCCTATTTGGTCCT 3' |
| C.LEU2.54 | 25 | 90 | 5' TTCTGCCCGCCTCCTTCCGACGAGATAGGCGGACACCGCTTTCATGGCCCTACAACATGAGCCACCATTGCCTATTTGGTCCTTGGATAA 3' |
| C.LEU2.40 | 26 | 76 | 5' TTCTGCCCGCCTCCTTCCGACGAGATAGGCGGACACATGGCCCTACAACATGAGCCACCATTGCCTATTTGGTCCT 3' |
| A4.TRP5.54 | 27 | 82 | 5' TGAAGGCCAAAACGGCTGAATCGATAGTGGAAAAGGGTTTTGATGAAGCTGTCGCGGATCCCACATTCTGGGAAGACTTCAA 3' |
| NT.TRP5.40 | 28 | 40 | 5' GGTTTTGATGAAGCTGTCGCGGATCCCACATTCTGGGAAG 3' |
| NT.ADE2.40 | 29 | 40 | 5' ATGGCCCTACAACATGAGCCACCATTGCCTATTTGGTCCT 3' |
| NT.LEU2.40 | 29 | 40 | 5' ATGGCCCTACAACATGAGCCACCATTGCCTATTTGGTCCT 3' |

TABLE 1-continued (Supplementary Table 1) Oligonucleotides used in this study

| Name | SEQ ID NO: | Size | Sequence |
|---|---|---|---|
| | | | Mammalian Oligos |
| A7.Red.54 | 30 | 90 | 5' GCGGGCGCTGTTGACAGCGGTCAGGTGGATGGGATGGCGACCGTGACCCAGGACT |
| A7.Red.40 | 31 | 76 | 5' GCGGGCGCTGTTGACAGCGGTCAGGTGGATGGGATGTGACCCAGGACTCCTCCCTG CAGGACGGCTGCTTCATCTA |
| A7.Red.30 | 32 | 66 | 5' GCGGGCGTGTTGACAGCGGTCAGGTGGATGGGATGCAGGACTCCTCCCTGCAGG ACGGCTGCTTC 3' |
| C.Red.54 | 33 | 90 | 5' TTTCTTGCCCGCCTCCTTCCGACGAGATAGGCGGACACGCGACCGTGACCCAGGACTCCTCCCTGCAGGACGGCTGCTT |
| C.Red.40 | 34 | 76 | 5' TTCTGCCCGCCTCCTTCCGACGAGATAGGCGGACACTGACC |
| C.Red.30 | 35 | 66 | 5' TTCTGCCCGCCTCCTTCCGACGAGATAGGCGGACACCAGGA |
| NT.Red.40 | 36 | 40 | 5' TGACCCAGGACTCCTCCCTGCAGGACGGCTGCTTCATCTA 3' |
| NT.Red.30 | 37 | 30 | 5' CAGGACTCCTCCCTGCAGGACGGCTGCTTC 3' |

Shown are the oligonucleotides used in the aptamer selection, yeast experiments, and mammalian experiments. The aptamer sequences are underlined.

TABLE 2

(Supplementary Table 2) Strains used for yeast studies

| Strain Name (nickname) | Relevant Genotype | Source |
|---|---|---|
| BY4742 | MATα his3Δ1 leu2Δ0 lys2Δ0 ura3Δ0 | (3) |
| FRO-155(TSB) | BY4742 (MATα his3Δ1 leu2Δ0 lys2Δ0 ura3Δ0 trp5::I-SceI site-GSHU lys2::Alu IR) contains the I-SceI site-GSHU cassette (I-SceI site, I-SceI gene under GAL1 promoter, hygromycin-resistance gene hyg, the counterselectable KlURA3) and the I-SceI site (HOT site) in trp5 | (3) |
| FRO-156(TSB) | MATα his3Δ1 leu2Δ0 lys2Δ0 ura3Δ0 trp5::I-SceI site-GSHU lys2::Alu IR | (3) |
| FRO-526(T5) | MATα his3Δ1 leu2Δ0 lys2Δ0 ura3Δ0 trp5::UK contains the UK cassette (the counterselectable KlURA3 and KanMX4 for G418$^R$) | (3) |
| FRO-527(T5) | MATα his3Δ1 leu2Δ0 lys2Δ0 ura3Δ0 trp5::UK | (3) |
| PAT-44 | MATα his3Δ1 leu2Δ0 lys2Δ0 ura3Δ0 trp5::I-SceI site-GSHU lys2::Alu IR rad52Δ0 | This study |
| PAT-45 | MATα his3Δ1 leu2Δ0 lys2Δ0 ura3Δ0 trp5::I-SceI site-GSHU lys2::Alu IR rad52Δ0 | This study |
| PAT-32(A2B) | MATα his3Δ1 leu2Δ0 lys2Δ0 ura3Δ0 ade2::I-SceI site-GSH | This study |
| PAT-33(A2B) | MATα his3Δ1 leu2Δ0 lys2Δ0 ura3Δ0 ade2::I-SceI site-GSH | This study |
| PAT-42(A2) | MATα his3Δ1 leu2Δ0 lys2Δ0 ura3Δ0 ade2::GSH | This study |
| PAT-43(A2) | MATα his3Δ1 leu2Δ0 lys2Δ0 ura3Δ0 ade2::GSH | This study |
| PAT-34(L2B) | MATα his3Δ1 lys2Δ0 ura3Δ0 leu2::I-SceI site-GSH | This study |
| PAT-35(L2B) | MATα his3Δ1 lys2Δ0 ura3Δ0 leu2::I-SceI site-GSH | This study |
| PAT-36(L2B) | MATα his3Δ1 lys2Δ0 ura3Δ0 leu2::I-SceI site-GSH | This study |
| PAT-37(L2B) | MATα his3Δ1 lys2Δ0 ura3Δ0 leu2::I-SceI site-GSH | This study |
| PAT-38(L2) | MATα his3Δ1 lys2Δ0 ura3Δ0 leu2::GSH | This study |
| PAT-39(L2) | MATα his3Δ1 lys2Δ0 ura3Δ0 leu2::GSH | This study |
| PAT-40(L2) | MATα his3Δ1 lys2Δ0 ura3Δ0 leu2::GSH | This study |
| PAT-41(L2) | MATα his3Δ1 lys2Δ0 ura3Δ0 leu2::GSH | This study |
| 55R5-3C | MATa ura1 ω C$^R$ (omega chloramphenicol resistant) | (23) |
| PAT-18(T1B) | MATα ura1Δ0 trp1 ::I-SceI site-GSH | This study |
| PAT-19(T1B) | MATα ura1Δ0 trp1 ::I-SceI site-GSH | This study |

TABLE 2-continued (Supplementary Table 2) Strains used for yeast studies

| Strain Name (nickname) | Relevant Genotype | Source |
|---|---|---|
| PAT-24(T1) | MATα ura1Δ0 trp1::GSH | This study |
| PAT-25(T1) | MATα ura1Δ0 trp1::GSH | This study |
| PAT-20(L2B) | MATα ura1Δ0 leu2::I-SceI site-GSH | This study |
| PAT-21(L2B) | MATα ura1Δ0 leu2::I-SceI site-GSH | This study |
| BPL-1(L2B) | MATα ura1Δ0 leu2::I-SceI site-GSH | This study |
| BPL-2(L2B) | MATα ura1Δ0 leu2::I-SceI site-GSH | This study |
| PAT-26(L2) | MATα ura1Δ0 leu2::GSH | This study |
| PAT-27(L2) | MATα ura1Δ0 leu2::GSH | This study |
| BPL-4(L2) | MATα ura1Δ0 leu2::GSH | This study |
| BPL-5(L2) | MATα ura1Δ0 leu2::GSH | This study |
| PAT-22(A2B) | MATα ura1Δ0 ade2::I-SceI site-GSH | This study |
| PAT-23 (A2B) | MATα ura1Δ0 ade2::I-SceI site-GSH | This study |
| PAT-28(A2) | MATα ura1Δ0 ade2::I-SceI site-GSH | This study |
| PAT-29(A2) | MATα ura1Δ0 ade2::I-SceI site-GSH | This study |
| FRO-767 | leu2::HOcs1, mata ::hisG, ho , hml ::ADE1, | (24) |
| HK-225 (T5B(HO)) | FRO-767 his3::TRP1 leu2::ins2 trp5::HOcs | This study |
| HK-226(T5B(HO)) | FRO-767 his3::TRP1 leu2::ins trp5::HOcs | This study |

Shown are the yeast strains used in this study.
[1] HO cut site.
[2] The LEU2 open reading frame is replaced by an insert that contains an inverted copy of the his3 gene, which is expressed by the GAL1 promoter and is disrupted by an artificial intron, which contains 80 bp of the green fluorescent protein (GFP) gene. Such insertion is not relevant for this study.

TABLE 3

(Supplementary Table 3) Yeast transformation using A7 aptamer with primers

| Oligo | Break on Gal |
|---|---|
| No oligo (TRP5) | <0.5 (0-0) |
| P1-A7-P2.TRP5.40 | 2,620 (2,250-2,990) |
| TRP5.40.P1-A7-P2 | 0.73 (0.28-1.19) |

The frequency of Trp+ colonies per $10^7$ viable cells, with mean and 95% confidence intervals (in parentheses), of yeast transformations in the FRO-155 strain from the BY4742 background with the I-SceI gene and with the I-SceI site, using 114-mer oligonucleotides. Two repeats of the no oligo control were done and 6 repeats for the oligonucleotide transformations. Data presented in FIG. 2.

Data Presentation and Statistics

Graphs were made using GraphPad Prism 5 (Graphpad Software, La Jolla, Calif., USA). Data are plotted as mean values with 95% confidence intervals shown. Statistical significance was determined using nonparametric twotailed t-tests (Mann-Whitney U test).

Example 1

Yeast Transformation Data

TABLE 4

| A | | | |
|---|---|---|---|
| Oligo | Break on Gal | Break on Glu | No Site on Gal |
| No oligo (TRP5) | 0.54 (0-1.36) | <0.5 (0-0) | <0.5 (0-0) |
| A7.TRP5.54 | 62,500 (35,800-89,200) | 3.64 (1.00-6.28) | 0.16 (0.05-0.27) |
| C.TRP5.54 | 8,950 (4,170-13,700) | 1.21 (0-2.69) | 0.13 (0.03-0.23) |
| A4.TRP5.54 | 9,030 (2,120-15,900) | 2.09 (1.71-2.47) | <0.4 (0-0) |
| No oligo (ADE2) | <0.5 (0-0) | <0.5 (0-0) | <0.5 (0-0) |
| A7.ADE2.54 | 57,900 (41,500-74,300) | 15.4 (3.28-27.5) | 3.07 (0-7.01) |
| C.ADE2.54 | 18,200 (12,800-23,500) | 10.9 (0-22.9) | 5.03 (0-13.0) |
| No oligo (LEU2) | <0.5 (0-0) | <0.5 (0-0) | <0.5 (0-0) |
| A7.LEU2.54 | 522 (333-712) | 27.0 (17.1-36.9) | 3.61 (1.70-5.52) |
| C.LEU2.54 | 253 (163-343) | 21.0 (16.0-26.1) | 3.74 (1.77-5.71) |

| B | | | |
|---|---|---|---|
| Oligo | Break on Gal | Break on Glu | No Site on Glu |
| No oligo (TRP1) | <0.2 (0-0) | <0.2 (0-0) | 0.2 (0-0) |
| A7.TRP1.54 | 25.8 (18.7-32.8) | 10.8 (7.10-14.5) | 2.23 (−0-01-4.48) |
| C.TRP1.54 | 10.7 (5.77-15.7) | 8.75 (4.91-12.6) | 4.56 (1.47-7.66) |
| No oligo (ADE2) | <0.2 (0-0) | <0.5 (0-0) | <1 (0-0) |
| A7.ADE2.54 | 46.2 (39.4-53.0) | <0.2 (0-0) | <0.4 (0-0) |
| C.ADE2.54 | 15.4 (11.9-18.8) | <0.2 (0-0) | <0.4 (0-0) |

TABLE 4-continued

| | | | |
|---|---|---|---|
| No oligo (LEU2) | <0.2 (0-00) | 0.69 (0-3.64) | 0.4 (0-0) |
| A7.LEU2.54 | 97.1 (73.3-121) | 12.8 (457-21.1) | 8.92 (5.88-12.0) |
| C.LEU2.54 | 61.8 (50.4-73.2) | 12.5 (4.96-20.0) | 7.90 (5.38-10.4) |

In Table 4 (A) the frequency of transformant colonies per $10^7$ viable cells, with mean and 95% confidence intervals (in parentheses), of yeast transformations in strains from the BY4742 background. For the strains with I-SceI expression and the I-SceI site (Break on Gal), 12 to 18 repeats of each transformation were performed (with the exception of the negative controls, for the trp5 locus no oligo control there were 6 repeats, and for the ade2 locus and leu2 locus no oligo controls there were 3 repeats). Data presented in FIG. 3A. For the strains without the I-SceI site present (and in the case of the trp5 locus, no I-SceI gene) and grown on galactose media (No Site on Gal), 8 to 12 repeats were performed of each transformation, except for the no oligo controls and the A4.TRP5.54 oligonucleotide, which were repeated 3 times. Data presented in FIG. 3B. For the strains with the I-SceI gene and site, but grown on glucose media such that no I-SceI protein would be expressed (Break on Glu), 4 repeats of the A7.TRP5.54 and C.TRP5.54 oligonucleotides were performed and 7 repeats of the A4.TRP5.54 oligonucleotide was performed for the trp5 locus. For the ade2 and leu2 loci, 12 repeats of the A7 aptamer containing oligonucleotide (the A4 aptamer was not tested at these loci) and the non-binding control containing oligonucleotide were used. Two repeats of the no oligo control were performed for the trp5 and ade2 loci, while 3 repeats of the no oligo control were performed for the leu2 locus. Data presented in FIG. 3C.

In Table 4 (B) the frequency of transformant colonies per $10^7$ viable cells, with mean and 95% confidence intervals (in parentheses), of yeast transformations in strains from the 55R5-3C background with or without the I-SceI gene and with or without the I-SceI site. For the strains with I-SceI expression and the I-SceI site (Break on Gal), 23 to 29 repeats of each transformation were performed (with the exception of the negative controls, for the trp1 locus no oligo control there were 7 repeats, for the ade2 locus there were 6 repeats, and for the leu2 locus no oligo controls there were 5 repeats). Data presented in FIG. 4A. For the strains without the I-SceI site present and grown on glucose media (No Site on Glu), 25 repeats were performed of each transformation for the trp1 locus, except for the no oligo control which was repeated 5 times. For the ade2 locus, 3 repeats of the transformations were done and one repeat of the no oligo control. For the leu2 locus, 9 repeats of each of the transformations were done and 3 repeats of the no oligo control.

Figures 4A, 4B, 4C:
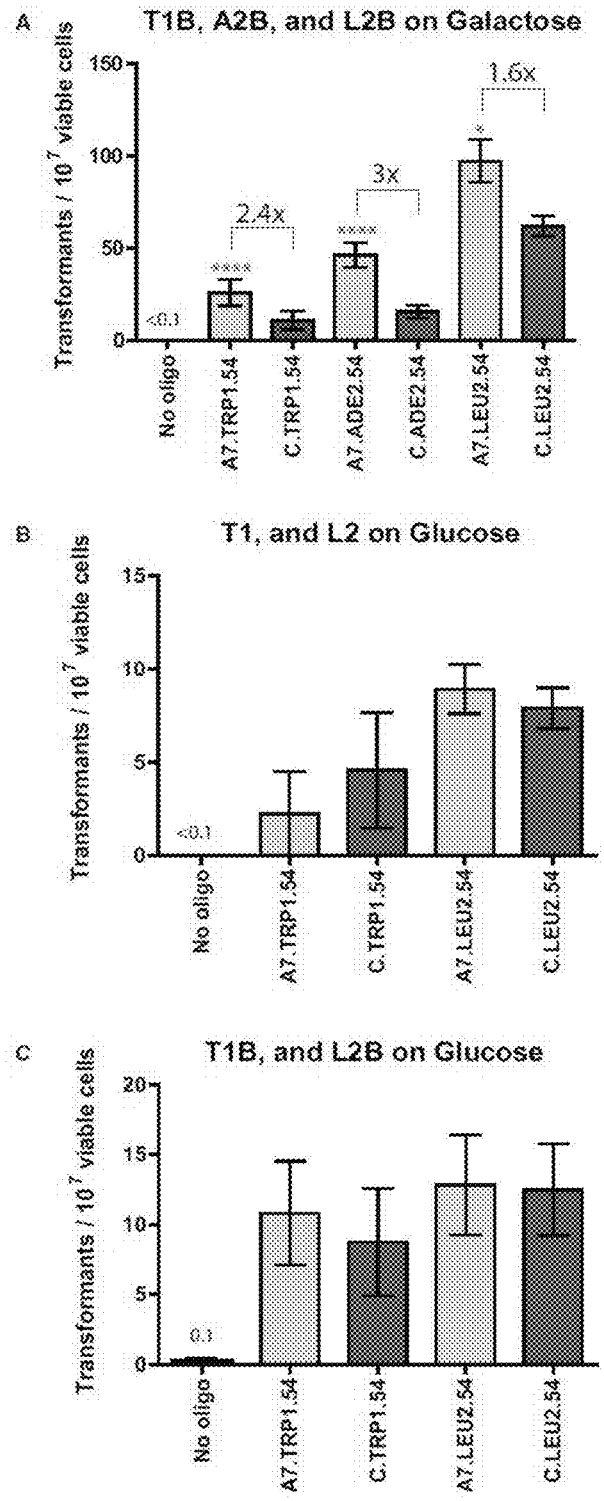
FIGS. 4A-4C show that the I-SceI aptamer stimulates gene targeting in yeast strain background 55R5-3C. Frequency of gene correction in yeast using oligonucleotides with aptamer-containing oligonucleotides in light grey and non-binding control oligonucleotides in dark grey (X axis) measured by the number of transformants per $10^7$ viable cells (Y axis) with no oligonucleotide controls averaged in (4A) strains from the 55R5-3C background containing the I-SceI break site as well as the I-SceI gene under the GAL1-10 promoter grown on galactose media (T1B, A2B, and L2B on galactose), (4B) strains that did not contain the I-SceI site grown on glucose containing media (T1, A2, and L2 on glucose), (4C) same strains shown in 4A) but grown on glucose-containing media (T1B, A2B or L2B on glucose). For both (4B) and (4C), the frequency of gene correction for the ade2 locus was <0.2 and <0.4, respectively (not shown). Bars correspond to the mean value and error bars represent 95% confidence intervals. Asterisks denote statistical significant difference between the aptamer-containing oligonucleotide and the corresponding non-binding control (*P<0.05; P<0.01; *P<0.001 and ****P<0.0001), and the fold change in the gene correction frequency is indicated.

Data presented in FIG. 4B. For the strains with the I-SceI gene and site, but grown on glucose media such that no I-SceI protein would be expressed (Break on Glu), 25 repeats of the A7.TRP1.54 and C.TRP1.54 oligo were performed for the trp1 locus, 6 repeats of A7.ADE2.54 and C.ADE2.54 were performed for the ade2 locus, and 9 repeats for the leu2 locus. Two repeats of the no oligo control were performed for the ade2 locus, while 3 repeats of the no oligo control was performed for the leu2 locus, and 5 repeats of the no oligo control was done for the trp1 locus. Data presented in FIG. 4C.

Example 2

Selection for an Aptamer to I-SceI

A fluorescently-labelled DNA library consisting of singlestranded 74-mer oligonucleotides containing a central 36-nt variable region (Table 1) was loaded with I-SceI protein on CE with LIF. Two rounds of selection were done to obtain DNA aptamers to I-SceI. Several potential aptamers from the selection pool of aptamers were again run with I-SceI and weak, moderate and strong binding aptamers were identified. The 17 strongest binding aptamers identified were selected for sequencing. Several of the sequences were repeated, such that there were only 11 unique strong binding aptamer sequences (Table 1), which showed no general consensus sequence. Of the 11 unique sequences, only three contained the original length of the aptamer region, 36 bases, from the random DNA library. The difference in sequence length from the starting library is not uncommon in aptamer selection (Mahlknecht, et al., *Proc. Natl Acad. Sci. USA*, 110:8170-8175 (2013); McKeague, et al., *Int. J. Mol. Sci.*, 11:4864-4881 (2010); Kiga, et al., *Nucleic Acids Res.*, 26:1755-1760 (1998)).

After sequencing the 11 strongest binding aptamers, these candidate aptamers were further characterized using EMSA gels to confirm their binding capacity to I-SceI. Of the candidate aptamers, several showed consistent and reproducible binding to I-SceI. Of these, two sequences were chosen to design synthetic oligonucleotides based on their length and their ability to bind to I-SceI, namely, I-SceI aptamer 4 (A4), which was 28 nucleotides, and I-SceI aptamer 7 (A7), which was 36 nucleotides. These two oligonucleotides were synthesized polyacrylamide gel electrophoresis (PAGE) purified, FAM-labelled for fluorescence and underwent further testing by CE with LIF. The binding affinities by CE were calculated to be about 3.16 µM for A7 (FIG. 9D) and about 52.49 µM for A4 (not shown), by a method described previously (Berezovski, et al., *J. Am. Chem. Soc.*, 124:13674-13675 (2002)); thus, it appeared that A7 was a stronger binder to I-SceI than A4.

TABLE 5

(Table 1). Aptamer sequences to I-SceI

| Name | Size | Sequence |
|---|---|---|
| A1 | 17 | TCAGTTCCTTGGTTAGG (SEQ ID NO: 38) |
| A3 | 36 | TCTAAGACTTGTGAGTCATACGGTGGGACGCGGTAA (SEQ ID NO: 39) |
| A4 | 28 | TGAAGGCCAAAACGGCTGAATCGATAGT (SEQ ID NO: 40) |
| A5 | 26 | GCCTTGCTTGAACTGGTAGCACATGT (SEQ ID NO: 41) |
| A6 | 51 | CTCCTGGTCTAGACGAGCCTCACTTTCCAAATCATGAC GAGATAGGCGGAC (SEQ ID NO: 42) |

TABLE 5 -continued (Table 1). Aptamer sequences to I-SceI

| Name | Size | Sequence |
|---|---|---|
| A7 | 36 | GCGGGCGCTGTTGACAGCGGTCAGGTGGATGGGATG (SEQ ID NO: 43) |
| A8 | 35 | CTGCATTTCCTATGGACACAGTGCTTCGTTCAATC (SEQ ID NO: 44) |
| A9 | 35 | GAGTGCCGCGGGGACTGTCAAGTCGCTGGGTCTA (SEQ ID NO: 45) |
| A10 | 35 | AGGCAGACGCCTCTGACGCAAGGTGCATTGCCTTT (SEQ ID NO: 46) |
| A11 | 18 | ATGTGTATTTGCCAGTAA (SEQ ID NO: 47) |
| A18 | 36 | GTTGCGCTCTAGCTGATCGTGTTTATCCCAAAGGCA (SEQ ID NO: 48) |

Shown are the 11 strongest I-SceI aptamer sequences. The aptamer A4 and A7 chosen for further analysis are shown in bold. The A7 aptamer is also underlined.

Example 3

The I-SceI Aptamer Stimulates Gene Correction in Yeast

Figure 2:
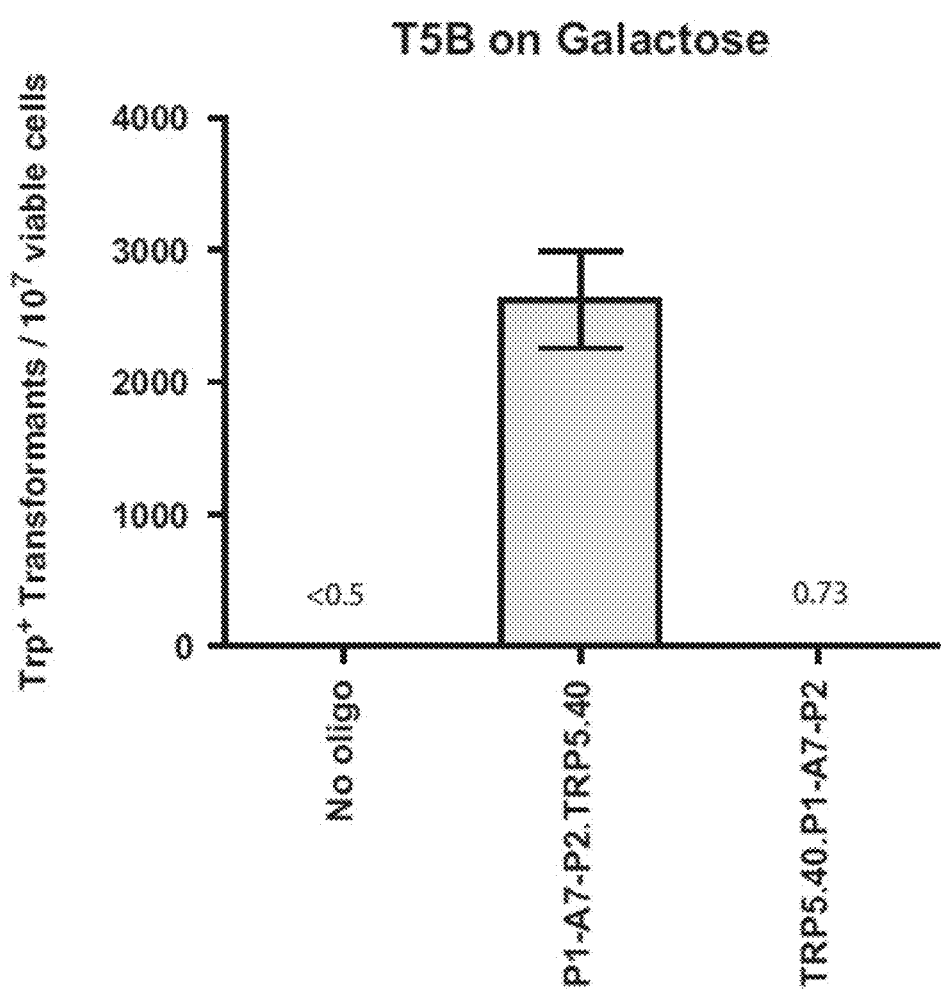
FIG. 2 is a bar graph showing that a bifunctional oligonucleotide with the I-SceI aptamer sequence at the 5' end and the donor sequence at 3' end is more effective at gene targeting in yeast. Frequency of gene correction in yeast by the A7 aptamer with primers from the random DNA library at either the 50 or 30 end of a longer oligonucleotide to repair the trp5 gene (X axis) measured by the number of Trp+ transformants per $10^7$ viable cells (Y axis) in the FRO-155 (T5B) strain plated to galactose media. Bars correspond to the mean value, and error bars represent 95% confidence intervals.

Experiments of gene correction were done in yeast *S. cerevisiae* cells using bifunctional single-stranded DNA oligonucleotides containing the aptamer region of the A4 or A7 I-SceI aptamer at one end, and the donor repairing sequence at the other end. First, we determined on which end (5' or 3') the I-SceI aptamer should be positioned in the bifunctional molecule to obtain more effective stimulation of gene targeting. For this experiment, the A7 aptamer with primers P1 and P2 from the random DNA library was synthesized as part of the 5' end or the 3' end of the repairing bifunctional oligonucleotides (P1-A7-P2.TRP5.40 for the aptamer with primers at the 50 end of the bifunctional oligonucleotide and TRP5.40.P1-A7-P2 for the aptamer at the 3' end) (Table 1), which contained 40 bases of homology to correct a disrupted TRP5 gene in yeast strain FRO-155/156 (T5B in FIG. 1) and restore function of the TRP5 gene. Results showed that having the aptamer region at the 5' end of the bifunctional molecule was much more efficient at gene targeting than with the aptamer region at the 3' end (FIG. 2). Likely, having the homology region of the donor sequence at the 3' end facilitates the homology search to the target locus, rather than being a polarity preference of the annealing protein Rad52 (Parsons, et al., *EMBO J.*, 19:4175-4181 (2000)). The aptamer-containing oligonucleotide with the primers (P1-A7-P2.TRP5.40) was compared with the non-binding random control with primers (P1-r-P2.TRP5.40), and there was a 1.25-fold (P=0.0008) increase using the aptamer-containing oligonucleotide (data not shown). The low increase in gene targeting for this experiment stems from the fact that I-SceI was induced before plating such that most cells already had the DSB before transformation with the oligonucleotides. For all subsequent experiments, I-SceI was induced by directly plating cells on the selective medium containing galactose.

Figures 3A, 3B, 3C, 3D:
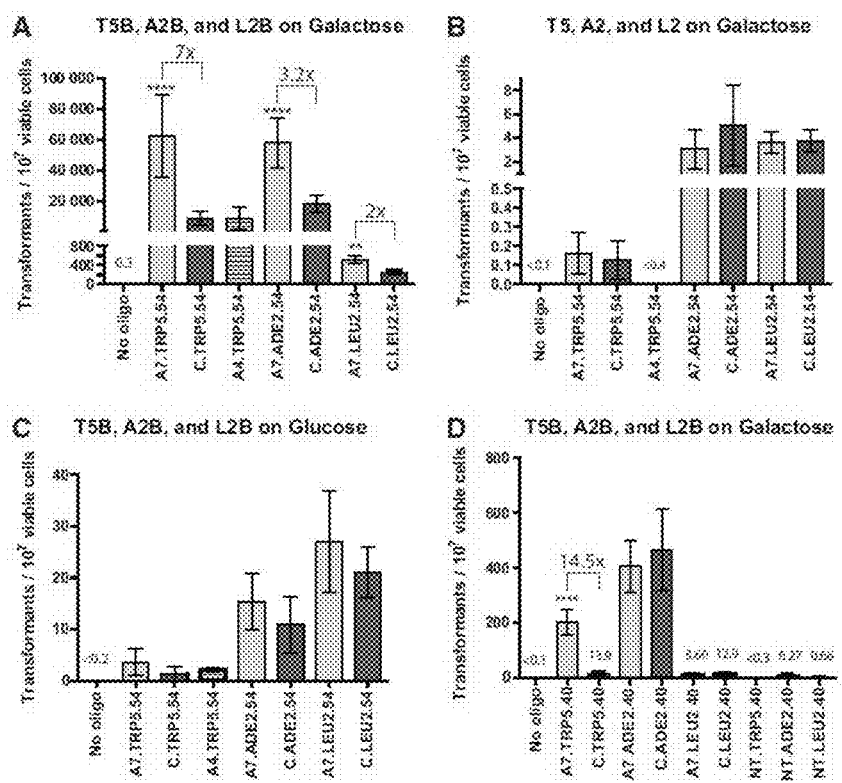
FIGS. 3A-3G show that the I-SceI aptamer stimulates gene targeting in yeast strain background BY4742. Frequency of gene correction in yeast using aptamer containing oligonucleotides shown in light grey and non-binding control oligonucleotides in dark gray (X axis) measured by the number of transformants per $10^7$ viable cells (Y axis) with no oligonucleotide controls averaged in (3A) strains from the BY4742 background containing the I-SceI break site and the I-SceI gene under the GAL1-10 promoter grown on galactose media (T5B, A2B and L2B on galactose), (3B) strains that did not contain the I-SceI site grown on galactose media (T5, A2, and L2 on galactose), (3C) same strains shown in (3A) but grown on glucose-containing media (T5B, A2B, and L2B on glucose). (3D) Frequency of gene correction in yeast by shorter targeting oligonucleotides with only 40 bases of homology, including oligonucleotides without a 5' non-homologous tail (no tail' NT.TRP5.40, NT.ADE2.40 and NT.LEU2.40) of the aptamer region or the non-binding control sequence. (3E) Frequency of gene correction in yeast by PAGE-purified oligonucleotides at the trp5 locus in the FRO-155/156 (T5B) strain grown on galactose for the induction of I-SceI. (3F) Frequency of gene correction following co-transformation of strains PAT-34 and PAT-35 (L2B), grown on galactose for I-SceI induction, with C.LEU2.54 or C.LEU2.40 with A7.TRP5.40 or C.TRP5.40. (3G) Frequency of gene correction in yeast by the A7.TRP5.40 or C.TRP5.40 oligonucleotides at the trp5 locus in the I-SceI containing strain FRO-155/156 (T5B) or in the HO-containing strain HK-225/226 [T5B(HO)] grown on galactose for the induction of I-SceI or HO, or on glucose for the repression of I-SceI or HO. Bars correspond to the mean value and error bars represent 95% confidence intervals. Asterisks denote statistical significant difference between the aptamer-containing oligonucleotide and the corresponding non-binding control (*P<0.05; P<0.01; *P<0.001 and ****P<0.0001), and the fold change in the gene correction frequency is indicated.

Previous studies of aptamer selection showed that the primer sequences from the random DNA library that flank the aptamer region in the SELEX process do not generally contribute to aptamer binding (Cowperthwaite, et al., *J. Mol. Evol.*, 67:95-102 (2008); Pan, et al., *Molecules*, 14:1353-1369 (2009); Legiewicz, et al., *RNA*, 11:1701-1709 (2005)), and they can be removed without affecting the binding function of the aptamer sequence. Therefore, we removed the primer regions surrounding the I-Sce I aptamer sequence in the bifunctional oligonucleotides, and this also allowed us to extend the sequence length of the gene-correction donor part of the bifunctional molecule. Oligonucleotides that contained the aptamer sequences from A4 or A7 at the 5' end of a DNA sequence containing 54 bases of homology to restore the disrupted trp5 gene (A4.TRP5.54 and A7.TRP5.54, Table 1) were tested in yeast strains FRO-155/156 and FRO-526/527 (T5B and T5 in FIG. 1) for their capacity to restore the functionality of the trp5 gene. In addition to the aptamer-containing oligonucleotides used to correct the trp5 gene a negative control oligonucleotide was used. Because of the inability of the library primers P1 and P2 to bind I-SceI, these were used in place of the aptamer sequence in a new sequence (C) as part of the non-binding negative control oligonucleotide used to repair trp5 (C.TRP5.54) (Table 1). Using the A4 or A7 aptamer-containing oligonucleotides to repair the trp5 gene, it was found that the A7 aptamer containing oligonucleotide (A7.TRP5.54) significantly increased (P<0.0001) the level of gene correction 7-fold compared with the negative control (C.TRP5.54) or the other aptamer-containing oligonucleotide A4.TRP5.54 (P<0.0001) in the FRO-155/156 strain, in which the I-SceI gene was expressed and the I-SceI site was present at the target site (T5B in FIG. 3A). FRO-526, the strain that did not have the I-SceI site and also did not express the I-SceI gene (T5 in FIG. 3B), showed no significant difference between the A7 aptamer-containing oligonucleotide A7.TRP5.54, the A4 aptamer-containing oligonucleotide A4.TRP5.54 (P=0.2161) or the negative control C.TRP5.54 (P=0.702). As an additional control, FRO-155/156 (T5B) was grown and plated to glucose-containing media. Without galactose induction for the expression of I-SceI, there was no significant difference between the aptamer-containing oligonucleotide A7.TRP5.54 and the negative control C.TRP5.54 (P=0.814) or the other aptamer-containing oligonucleotide A4.TRP5.54 (P=0.109) (FIG. 3C). These controls refute the possibility that the aptamer (A7) sequence is simply protecting the oligonucleotide from degradation better than the non-binding control sequence (C). If the non-binding control sequence did not protect the repair template as effectively as A7, then one would expect that the control sequence would consistently be lower in gene targeting efficiency than the A7 aptamer, which is not the case when the I-SceI site is not present or when the I-SceI protein is not expressed.

Example 4

Figures 3E, 3F, 3G:
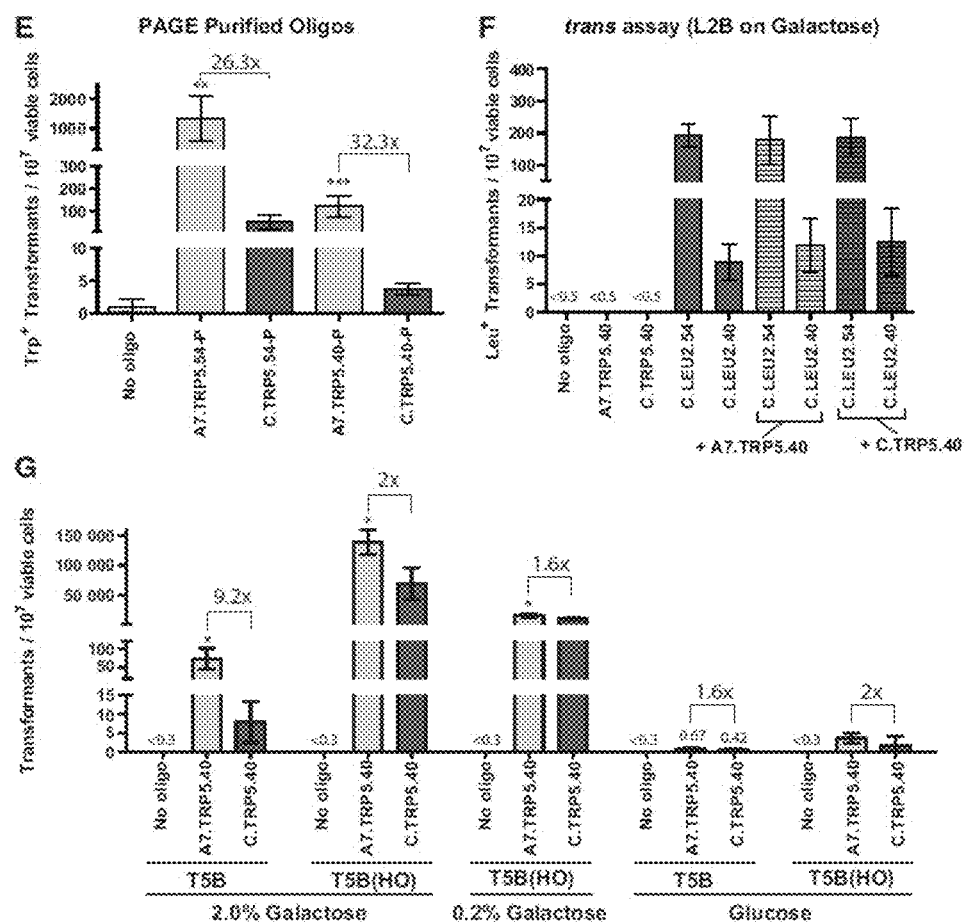

Gene Targeting Stimulation by the I-SceI Aptamer is More Effective for a Donor with Short Homology Although decreasing the donor's region of homology generally leads to less efficient gene correction (Storici, et al., *Proc. Natl Acad. Sci. USA*, 100:14994-14999 (2003)), it was postulated that it might be possible to detect an even greater fold-difference in gene correction efficiency from the aptamer-containing oligonucleotide over the nonbinding control if the aptamer was attached to a shorter donor. By shortening the donor homology region of the A7.TRP5.54 bifunctional oligonucleotide from 54 bases to 40 bases (A7.TRP5.40), the overall frequency of repair decreased as expected. However, the frequency of repair at the trp5 locus using the shorter donor showed an even greater fold difference between the A7 aptamer-containing oligonucleotide and the non-binding negative control (from 7-fold to 15-fold) (P<0.0001) (FIG. 3D). Oligonucleotides that contained neither the aptamer region nor the control non-binding sequence [no 5' nonhomologous 'tail' (NT in FIG. 3D)] were inefficient at targeting (FIG. 3D) because without the 5' non-homologous DNA the oligonucleotide donor sequence was less stable [Storici, F., unpublished data and (24)]. Similarly, the overall repair frequency of the A7.TRP5.40 oligonucleotide was lower than that of the P1-A7-P2.TRP5.40 oligonucleotide due to the greater lengths of the P1-A7-P2.TRP5.40 oligonucleotide (FIGS. 2 and 3D). A possible reason for the increased difference in gene correction frequency between the aptamer-containing molecule and the control molecule could also be that the shorter oligonucleotides were more likely to have the aptamer region intact. Non-purified 100-mer oligonucleotides synthesized at a coupling efficiency of 99.5% contain about 60% full-length product, with the other 40% being truncated oligonucleotides (Stafford, et al., *Nucleic Acids Res.*, 35:e72 (2007)) (truncated at the 50 end of the oligonucleotide, which in our system would be the aptamer region). Based on the idea that full-length oligonucleotides would have higher likelihood to contain the intact aptamer region, polyacrylamide gel electrophoresis (PAGE)-purified oligonucleotides were tested at the trp5 locus in yeast strain FRO-155. The PAGE-purified oligonucleotides showed a greater fold difference in repair of trp5 with the aptamer oligonucleotide as compared with the control than the non-purified oligonucleotides (FIG. 3E). Although the fold difference between the aptamer and the control was higher in the purified oligonucleotides [27-fold (P=0.0057) for A7.TRP5.54-P and 32-fold (P=0.0004) for A7.TRP5.40-P], the fold difference of the shorter oligonucleotide (A7.TRP5.40-P) was still more prominent than the longer oligonucleotide (A7.TRP5.54-P). These results suggest the aptamer can be more effective with a shorter homology region.

Example 5

Aptamer-Guided Gene Targeting is Effective at Numerous Different Targeted Genomic Loci in Yeast The effectiveness of AGT with the I-SceI aptamer was tested at numerous other loci in the yeast genome to verify that the results obtained at the trp5 gene were not locus specific. In these new loci, the A7 aptamer was compared with the non-binding control (C). Because aptamer A4 was not increasing gene targeting (likely due to its lower binding affinity to I-SceI) at the trp5 locus, it was not used at other loci. At each of these loci, the GSH cassette containing the I-SceI gene under the inducible GAL1-10 promoter along with the hygromycin resistance gene hyg were integrated into different endogenous marker genes responsible for the metabolism of nucleotides or amino acids, generating auxotrophic mutants for the respective nucleotide or amino acid. The ADE2 and LEU2 loci were chosen as targets in the BY4742 strain background, and the TRP1, ADE2 and LEU2 loci were chosen in the 55R5-3C strain background (FIG. 1). For each locus, two types of strains were made in which one had the integrated GSH cassette with the 18-bp I-SceI recognition site (T1B, A2B and L2B in FIG. 1) and one strain that had the cassette but did not have the I-SceI site (T1, A2 and L2 in FIG. 1) (see 'Materials and Methods' section). Following transformation by the bifunctional oligonucleotides with the aptamer for I-SceI or the control region, at every locus tested, using two or more isogenic strain isolates, there was a significant increase in gene targeting with the aptamer-containing (A7) oligonucleotide compared with the negative control (C) oligonucleotide when I-SceI was induced by galactose and the I-SceI site was present (FIGS. 3A and 4A). There was about 3-fold increase for the ade2 locus (P<0.0001 for both BY4742 and 55R5-3C), about 2-fold increase for the leu2 locus (P=0.0074 for BY4742 and P=0.0175 for 55R5-3C) and about 2.5-fold for the trp1 locus (P<0.0001). Gene correction frequencies in strain 55R5-3C are lower than in BY4742 strain. This could be due to the strain to strain variation because the cassettes used to induce the DSB were the same for the two strains. Despite this difference in the level of correction frequency, the I-SceI aptamer stimulates gene targeting in both strains. Importantly, in the strains lacking the I-SceI site there was no significant difference between the aptamer containing (A7) and non-binding (C) oligonucleotides (FIGS. 3B and 4B) (P=1 for the ade2 locus, and P=0.9297 for the leu2 locus in the BY4742 background and P=0.185 for the trp1 locus, P=1 for the ade2 locus and P=0.5076 for the leu2 locus in the 55R5-3C background). Likewise, when the strains containing the I-SceI site were grown and plated to glucose-containing media, there was no significant difference between the aptamer containing (A7) and non-binding (C) oligonucleotides (P=0.4382 for the ade2 locus, and P=0.1907 for the leu2 locus in the BY4742 background and P=0.3581 for the trp1 locus, P=1 for the ade2 locus and P=0.8252 for the leu2 locus in the 55R5-3C background) (FIGS. 3C and 4C).

For the ade2 and leu2 loci in the BY4742 strain background by shortening the homology region from 54 to 40 bases, the overall level of repair decreased, similarly to the results at the trp5 locus. While the shorter aptamer containing oligonucleotide at the trp5 locus showed a greater fold increase over the non-binding control, no significant difference between the aptamer and the non-binding control oligonucleotides was observed for targeting at the ade2 or the leu2 loci using the shorter form of the oligonucleotides (FIG. 3D). In addition to shortening the donor length, oligonucleotides were tested in which there was no 5' non-homologous 'tail' (NT) that did not contain the aptamer or the non-binding control sequence but only the homology region for gene correction. Each of these oligonucleotides (NT.ADE2.40 and NT.LEU2.40) had very low gene correction frequency (FIG. 3D).

Example 6

The I-SceI Aptamer Stimulates Gene Targeting in Cis

To exclude the possibility that the aptamer binding to I-SceI could change the structure of I-SceI such that the function of I-SceI would be enhanced, therefore stimulating gene targeting of the donor molecule in trans, we performed the following experiment. The L2B strains were transformed in the BY4742 background that contain the I-SceI gene and the I-SceI site with the C.LEU2.54 or the C.LEU2.40 oligonucleotide, each in combination with either the A7.TRP5.40 or the C.TRP5.40 oligonucleotide. Among the aptamer-containing oligonucleotides tested in yeast, the A7.TRP5.40 showed the highest fold-difference over the non-binding control (C.TRP5.40) (FIG. 3 D). Because both the A7.TRP5.40 and C.TRP5.40 have no capability to repair the leu2 locus, it was envisioned that if the A7.TRP5.40 had stimulated donor targeting in trans at the trp5 locus, A7.TRP5.40 should also stimulate donor targeting at the leu2 locus by C.LEU2.54 or C.LEU2.40. In this experiment, the C.TRP5.40 would serve as a negative control to A7.TRP5.40 because it does not bind to I-SceI. Co-transformation of C.LEU2.54 or C.LEU2.40 with A7.TRP5.40 did not result in higher frequency of correction than using C.TRP5.40 (P=0.6424 for C.LEU2.54 and P=1 for C.LEU2.40) (FIG. 3F). These data support the conclusion that the I-SceI aptamer acts in cis with the donor region on the same bifunctional oligonucleotides to stimulate gene targeting. This result also contradicts the possibility that the aptamer binding to I-SceI could be inhibiting I-SceI function to bind or cleave. Aptamer inhibition of DNA binding and/or cleavage by I-SceI would lead to a decrease in gene repair, but cotransformation with A7.TRP5.40 had no effect on leu2 repair frequency.

Example 7

I-SceI Aptamer Stimulates Gene Targeting Only in the Presence of I-SceI and its Cut Site To verify the specificity of the I-SceI aptamer, an experiment was designed to test whether the I-SceI aptamer promoted gene targeting only in the presence of I-SceI endonuclease and its cut site or was able to stimulate gene correction also when a different homing endonuclease was expressed and its cut site replaced the I-SceI cut site in the yeast trp5 locus. A strain (FRO-767) that expresses the HO endonuclease under the GAL1 inducible promoter and which was previously used to study DSB repair by synthetic oligonucleotides was modified (Storici, et al., Nature, 447: 338-341 (2007)). By engineering FRO-767, strains HK-225 and HK-226 we constructed, which contain the HO cut site in the middle of the TRP5 gene in the exact same locus in which the I-SceI site was inserted in our strains [T5B(HO)] (FIG. 1). Strains FRO-155/156 (T5B) were transformed with the I-SceI endonuclease and its cut site, and HK-225/226 [T5B(HO)] with the HO endonuclease and its cut site using the bifunctional oligonucleotides with the aptamer for I-SceI (A7.TRP5.40) or the control sequence (C.TRP5.40). Cells were incubated in the presence of either 2% galactose to induce the expression of the I-SceI or HO endonuclease, or 2% glucose to repress the expression of the I-SceI or HO endonuclease. For the expression of the HO endonuclease, 0.2% galactose was used because HO is much more efficient than I-SceI for induction of the DSB [(Storici, et al., Nature, 447:338-341 (2007)) and this work]. Results presented in FIG. 3G show that the A7 I-SceI aptamer strongly stimulated gene correction over the control oligonucleotide (9.2-fold by mean comparison; P=0.0286) at the trp5 locus only with induction of I-SceI by galactose and when the I-SceI cut site was present. Differently, the A7 I-SceI aptamer increased gene correction 1.6-2-fold over the control oligonucleotide with induction of HO by galactose and when the HO cut site was present. Although not statistically significant, a similar 1.6-2-fold effect for the A7 I-SceI aptamer over the control oligonucleotide was also detected in glucose for the I-SceI and HO strains, respectively (FIG. 3G and Table 9). Thus, while there may be a slight effect by the aptamer alone, it is only the expression of I-SceI, and not HO, that activates the aptamer function of the A7 sequence to stimulate gene targeting by the A7.TRP5.40 oligonucleotide. These results demonstrate that the I-SceI aptamer does not simply stabilize the donor DNA sequence and that most of its stimulatory effect to promote gene correction is specific to I-SceI.

Example 8

AGT relies on Rad52

In a rad52-null FRO-155 background strain, repair of trp5 was much less efficient (FIG. 10) than in wild-type RAD52 cells (FIG. 3A). Comparing the repair level of A7.TRP5.54 in rad52 and RAD52 cells, there is a significant (P<0.0001) 20 000-fold decrease in the rad52-null background. Similarly, correction frequency by the control C.TRP5.54 oligonucleotide also drops several thousand fold. The rad52 strain had a high level of prototrophic clones occurring with no oligonucleotide addition. This is consistent with an increased frequency of large deletions at a DSB site by NHEJ in a rad52-null compared with a wild-type RAD52 background (Yu, et al., Genetics, 163:843-856 (2003)) that after ligation restore the function of the initially disrupted marker gene. Despite the high background level of repair in the rad52-null strain, there was a significant (P=0.0261) difference between the no oligonucleotide control and the aptamer-containing oligonucleotide, but there was no significant difference between the no oligonucleotide control and the non-binding control oligonucleotide (P=0.2432), suggesting that the aptamer may stimulate gene targeting even in the absence of Rad52. However, there was no significant difference between the non-binding control oligonucleotide and the aptamer-containing oligonucleotide (P=0.6902).

Example 9

I-SceI Aptamer Stimulates Gene Targeting in Human Cells

In addition to the in vivo testing in yeast, the ability of the A7 I-SceI aptamer to stimulate gene targeting in human embryonic kidney (HEK-293) cells was investigated. The defective marker gene we used was for the red fluorescent protein (RFP), DsRed2, with the DsRed2 gene carried on a plasmid, pLDSLm. Episomal plasmid substrates are valuable tools to study mechanisms of gene correction in human cells. An I-SceI recognition site and two stop codons disrupted the function of DsRed2. In addition to the targeted plasmid, bifunctional oligonucleotides were transfected along with an I-SceI expression vector, pSce, to repair the DSB generated by the I-SceI nuclease and restore the function of the DsRed2 gene. Similarly to the studies in yeast, we used bifunctional oligonucleotides that contained the A7 aptamer sequence at the 50 end or a nonbinding control sequence of equal length, and a donor sequence of 54 nt with homology to the DsRed2 gene at the 3' end. As in yeast, the non-binding control consisted of the primers from the random DNA library shown not to influence binding to I-SceI.

Figures 5A, 5B, 5C:
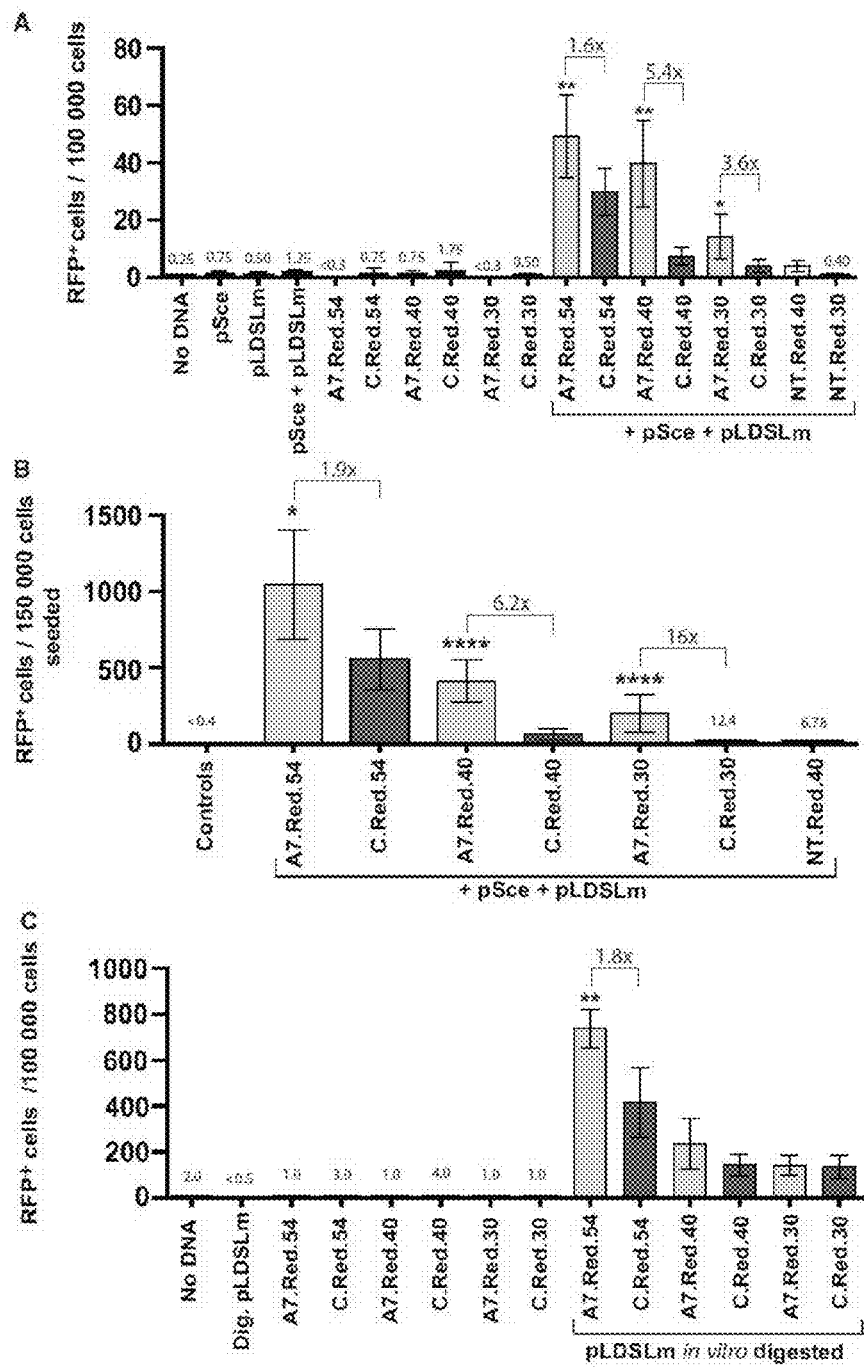
FIGS. 5A-5C show that the I-SceI aptamer stimulates gene targeting at the DsRed2 locus in human cells. (5A) Flow cytometry analysis of several transfections in HEK-293 cells, the different samples are shown on the X axis with aptamer-containing oligonucleotides in light grey and non-binding control oligonucleotides in dark grey and the number of RFP+ cells per 100 000 cells is shown on the Y axis. Negative controls were the cells alone (no DNA, only transfection reagent alone), the I-SceI expression vector alone (pSce), the targeted vector (pLDSLm) that contained the DsRed2 gene disrupted with two stop codons and the I-SceI site alone and the individual oligonucleotides alone. Transfections of oligonucleotides with both pSce and pLDSLm added are bracketed. (5B) Hand counts of each transfection were done in HEK-293 cells in lieu of flow cytometry, which was overreporting the number of background RFP+ cells for the shorter oligonucleotides. The different samples are shown on the X axis and the number of RFP+ cells per 150 000 cells seeded is shown on the Y axis. Negative controls did not show any RFP+ cells. (5C) Flow cytometry analysis of transfections of the in vitro digested pLDSLm vector, the different samples shown on the X axis and the number of RFP+ cells per 100 000 cells is shown on the Y axis. Negative controls were the cells alone (no DNA), the digested vector alone and the individual oligonucleotides alone. Transfections with both the digested vector and an oligonucleotide are bracketed. Bars correspond to the mean value and error bars represent 95% confidence intervals. Asterisks denote statistical significant difference between the aptamer-containing oligonucleotide and the corresponding non-binding control (*P<0.05; P<0.01; *P<0.001 and ****P<0.0001), and the fold change in the gene correction frequency is indicated.

Using an oligonucleotide containing the A7 aptamer and 54 bases of homology to DsRed2 (A7.Red.54), there was a significant (P=0.0012), about 2-fold, increase in repair over the non-binding control (FIG. 5A). As in yeast, oligonucleotides with shorter homology regions 30 to the aptamer or non-binding control sequence were designed and tested, using oligonucleotides with 40 or 30 bases of homology (Table 1). Similar to our results at the TRP5 locus in yeast, the shorter oligonucleotides with 40 bases of homology (A7.Red.40 and C.Red.40) had lower overall gene targeting frequency compared with the longer oligonucleotides (A7.Red.54 and C.Red.54) due to the decreased homology of these oligonucleotides. However, comparing repair of the A7.Red.40 oligonucleotide relative with the corresponding non-binding control oligonucleotide C.Red.40 (FIG. 5A), there was a 6-fold increase (P=0.0067) in gene targeting measured by flow cytometry. Comparing the A7.Red.30 and C.Red.30 oligonucleotides by flow cytometry, there was a 4-fold increase (P=0.0146). A high level of background was observed from the flow cytometer that we thought could be obscuring the fold difference seen with the aptamer-containing oligonucleotides over the non-binding control oligonucleotides, especially in the case of the shortest oligonucleotides, those with only 30 bases of homology to DsRed2. Using fluorescence microscopy, manual hand counts of the RFP$^+$ cells in each well were conducted (FIG. 5B), and for the oligonucleotides with 54 and 40 bases of homology, the hand counts and the readings by flow cytometry were in agreement, but for the A7.Red.30 oligonucleotide compared with the C.Red.30 oligonucleotide, a 16-fold increase (P<0.0001) in repair relative to the nonbinding control was observed instead of the 4-fold increase detected by flow cytometry.

AGT relies on the presence of the I-SceI protein to drive the aptamer-containing correction oligonucleotide to the targeted site, and without I-SceI expression there was no significant difference between the aptamer-containing oligonucleotides and the non-binding oligonucleotides in yeast. To verify the increase in gene targeting in human cells by AGT, the targeted vector (pLDSLm) was digested with I-SceI in vitro before transfection. By digesting the vector in vitro and without co-transfection of the I-SceI expression vector, the aptamer would not be able to be targeted to the I-SceI site by I-SceI. Following cotransfection of the linearized vector and the oligonucleotides, the overall frequency of RFP$^+$ cells increased for both the aptamer-containing and control oligonucleotides compared with experiments in which the I-SceI DSB was generated in vivo. This is expected because the I-SceI site had been efficiently cleaved before transfection by overnight in vitro digestion of the pLDSLm vector with excess I-SceI enzyme. Differently from the results obtained in human cells expressing I-SceI that are presented in FIGS. 5A and 5B, without the vector expressing I-SceI there was only a 1.6-fold difference (although not statistically significant, P=0.0952) between the A7.Red.40 and the non-binding C.Red.40 control, and no difference (P=1) between the A7.Red.30 and the non-binding C.Red.30 control (FIG. 5C). However, for the A7-aptamer containing oligonucleotide with 54 bases of homology to DsRed2 (A7.Red.54) compared with the non-binding control (C.Red.54), there was a significant 1.75-fold difference (P=0.0079). These data demonstrate that the increase in RFP$^+$ frequency observed for the shorter A7.Red.40 and A7.Red.30 oligonucleotides (6-fold for A7.Red.40, and 4-fold for A7.Red.30 or 16-fold with the hand counts for the same oligonucleotide) (FIGS. 5A and 5B) is due to the A7 aptamer sequence of these oligonucleotides, and it occurs only when the I-SceI protein is expressed in the targeted cells.

Example 10

I-SceI Aptamer Stem-Loop Secondary Structure is Important for I-SceI AGT

For the aptamer to bind to I-SceI, it must form a particular structure. The additional DNA needed for gene correction could potentially disrupt the aptamer structure. To investigate this possibility secondary structure prediction software mfold was used on all the oligonucleotides tested in yeast and human cells for gene correction to determine lowest free energy secondary structures under physiological conditions (see 'Materials and Methods' section). Using this program, the A7 aptamer with both primers from the DNA library shows a hairpin with a 4-nt loop that forms from the internal aptamer sequence (FIG. 6A). This hairpin was seen in both of the oligonucleotides (P1-A7-P2.TRP5.40 and TRP5.40.P1-A7-P2) used to determine which end (5' or 3') of the bifunctional oligonucleotide the aptamer region should be on (FIGS. 6B-D). The aptamer region without the primers showed a similar hairpin structure at its 5' end (FIG. 6E). The lowest free-energy (most stable) structures predicted for the bifunctional A7 aptamer-containing oligonucleotides in yeast with 54-base homology regions (A7.TRP5.54, A7.TRP1.54, A7.ADE2.54 and A7.LEU2.54) all formed this aptamer hairpin near the 5' end of the oligonucleotide (FIGS. 6F, H, I and K). It was interesting to note, however, that while the A7.TRP5.54, A7.TRP1.54 and A7.ADE2.54 oligonucleotides had several bases without secondary structure following the aptamer hairpin on the 3' side, the oligonucleotide to repair LEU2 (A7.LEU2.54) contained only a single base between the aptamer hairpin and another stem-loop structure. This might explain why the A7.LEU2.54 oligonucleotide, while still capable of increasing gene targeting, showed the least fold difference in repair over the non-binding control. When analysing the secondary structures of the A7 aptamer-containing oligonucleotides with 40 base homology regions (A7.TRP5.40, A7.ADE2.40 and A7.LEU2.40), there was no significant change in secondary structure for each of the oligonucleotides compared with the longer oligonucleotides, except for the A7.TRP5.40 oligonucleotide, which formed a stable stem loop structure but opposite to the aptamer hairpin (FIGS. 6G, 6J and 6L). Analyzing the predicted secondary structure of the bifunctional oligonucleotides to target DsRed2, we found that the DsRed2 aptamer-containing oligonucleotide with 54 bases of homology (A7.Red.54) was predicted to form the aptamer hairpin (FIG. 6M). Similar to the A7.LEU2.54 oligonucleotide, the A7.Red.54 oligonucleotide was predicted to have another large stem-loop structure close to the 3' end of the aptamer hairpin, and this would be consistent with the in vivo result that for the A7.Red.54 oligonucleotide the A7 aptamer is not facilitating gene targeting compared with the non-binding control in human cells via its specific interaction with I-SceI. If the A7 aptamer structure was unable to form for the A7.Red.54 oligonucleotide, it would explain the similar fold-difference over the nonbinding control with or without I-SceI expression (2-fold with I-SceI expression and 1.75-fold without). For the shorter oligonucleotides with 40 (A7.Red.40) or 30 (A7.Red.30) bases of homology to DsRed2 (FIGS. 6N and 6O), both were predicted to form the aptamer hairpin. The A7.Red.40 oligonucleotide is similar in structure to the A7.Red.54 oligonucleotide, except that the stem-loop predicted to form after the aptamer hairpin has a smaller loop region (7 bases compared with 13 bases), which may not interfere with the aptamer binding. Interestingly, the A7.Red.30 oligonucleotide, which had the highest fold difference compared with the non-binding control (C.Red.30) in human cells, had a secondary structure similar to that of the A7.TRP5.40 oligonucleotide, which showed the highest fold difference in yeast. Taken as a whole, these results provide relevant insights into oligonucleotide design for AGT. In the case of the I-SceI aptamer, the design of oligonucleotides to be most efficient for AGT is the one in which the aptamer stem-loop structure is intact and distant from other secondary structures. Although not employed here, the use of a linker between the aptamer and the homology regions might prove useful to ensure proper binding to I-SceI by the A7 aptamer.

Example 11

Yeast Transformations with Shorter Oligos

TABLE 6

| Oligo | Break on Gal | Oligo | Break on Gal |
| --- | --- | --- | --- |
| No oligo (TRP5) | <0.5 (0-0) | No oligo (ADE2) | <0.4 (0-0) |
| A7.TRP5.40 | 202 (155-248) | A7.ADE2.40 | 404 (311-496) |
| C.TRP5.40 | 13.9 (8.13-19.4) | C.ADE2.40 | 464 (316-612) |
| No oligo (LEU2) | <0.3 (0-0) | NT.TRP5.40 | <0.3 (0-0) |
| A7.LEU2.40 | 8.63 (5.84-11.4) | NT.ADE2.40 | 6.28 (2.18-10.4) |
| C.LEU2.40 | 12.89 (8.06-17.7) | NT.LEU2.40 | 0.66 (0-1.37) |

The frequency of transformant colonies per $10^7$ viable cells, with mean and 95% confidence intervals (in parentheses), of yeast transformations with strains from the BY4742 background containing both the I-SceI gene and the I-SceI site. The purpose of these experiments was to test oligonucleotides that contained the full length A7 aptamer but with a shorter homology region. For the no oligo controls, there were two repeats for the trp5 locus, three repeats for the ade2 locus, and four repeats for the leu2 locus. The transformations involving the oligonucleotides with 40 bases of homology were repeated 10 to 16 times, except for those oligonucleotides that contained only homology (NT.TRP5.54, NT.ADE2.54, and NT.LEU2.54) to the target locus, which were repeated 4 to 8 times. Data presented in FIG. 3D.

Example 12

PAGE Purified Oligonucleotides

TABLE 7

| Purified Oligo | Break on Gal |
| --- | --- |
| No oligo (TRP5) | 1.02 (0-2.21) |
| A7.TRP5.54-P | 1,340 (594-2,090) |

TABLE 7-continued

| Purified Oligo | Break on Gal |
| --- | --- |
| C.TRP5.54-P | 51.0 (16.5-85.5) |
| A7.TRP5.40-P | 122 (72.7-171) |
| C.TRP5.40-P | 3.78 (2.93-4.62) |

Polyacrylamide gel electrophoresis (PAGE) purified oligonucleotides were ordered and tested at the trp5 locus in the FRO-155 strain that contains both the I-SceI gene and the I-SceI site. The frequency of Trp+ colonies per 107 viable cells, with mean and 95% confidence intervals (in parentheses), of the yeast transformations are shown. The no oligo control was repeated 4 times and the oligonucleotide transformations were repeated 5 to 9 times. Data presented in FIG. 3E.

Example 12

Trans Assay

TABLE 8

| Oligo | Break on Gal |
| --- | --- |
| No oligo (LEU2) | <0.5 (0-0) |
| A7.TRP5.40 | <0.5 (0-0) |
| C.TRP5.40 | <0.5 (0-0) |
| C.LEU2.54 | 193 (172-221) |
| C.LEU2.40 | 8.89 (5.71-12.1) |
| A7.TRP5.40 + C.LEU2.54 | 178 (103-252) |
| A7.TRP5.40 + C.LEU2 .40 | 11.9 (7.07-16.6) |
| C.TRP5.40 + C.LEU2.54 | 186.9 (127-246) |
| C.TRP5.40 + C.LEU2.40 | 12.5 (6.52-18.4) |

Oligonucleotides tested at the leu2 locus in the PAT-34 and PAT-35 strains that contain both the I-SceI gene and the I-SceI site. The frequency of Leu+ colonies per $10^7$ viable cells, with mean and 95% confidence intervals (in parentheses), of the yeast transformations are shown. The controls (No oligo and the individual oligonucleotides) were repeated 2 times and the transformations with two oligonucleotides were repeated 8 times. Data presented in FIG. 3F.

Example 13

Specificity of the I-SceI Aptamer

TABLE 9

| | Break on 2.0% Gal | | Break on 0.2% Gal | Break on Glu | |
| --- | --- | --- | --- | --- | --- |
| Oligo | I-SceI | HO | HO | I-SceI | HO |
| No olio (TRP5) | <0.3 (0-0) | <0.3 (0-0) | <0.3 (0-0) | <0.3 (0-0) | <0.3 (0-0) |
| A7.TRP5.40 | 72.4 (44.4-100) | 138,487 (117,690-159,283) | 15,112 (12,525-17,701) | 0.67 (0.23-1.1) | 3.6 (2.3-5.0) |
| C.TRP5.40 | 7.9 (2.5-13.3) | 69.042 (42,236-95,849) | 9558 (7454-11,662) | 0.42 (0-0.93) | 1.8 (0-4.0) |

The frequency of Trp+ colonies per $10^7$ viable cells, with mean and 95% confidence intervals (in parentheses). All transformations were repeated 4 times. Data presented in FIG. 3G.

Example 14

DsRed2 Transfection Data

TABLE 10

| Transfected DNA | Flow Cytometry | Hand Counts |
|---|---|---|
| No DNA | 0.25 (0-0.84) | <0.4 (0-0) |
| pSce | 0.75 (0-1.55) | <0.4 (0-0) |
| pLDSLm | 0.50 (0-1.42) | <0.4 (0-0) |
| pSce + pLDSLm | 1.25 (0.45-2.05) | <0.4 (0-0) |
| A7.Red.54 | <0.3 (0-0) | <0.4 (0-0) |
| C.Red.54 | 0.75 (0-3.14) | <0.4 (0-0) |
| A7.Red.40 | 0.75 (0-2.27) | <0.4 (0-0) |
| C.Red.40 | 1.75 (0-5.28) | <0.4 (0-0) |
| A7.Red.30 | <0.3 (0-0) | <0.4 (0-0) |
| C.Red.30 | 0.5 (0-1.42) | <0.4 (0-0) |
| A7.Red.54 | 49.3 (34.8-63.8) | 1,040 (689-1,400) |
| C.Red.54 | 30.0 (21.7-38.2) | 554 (355-753) |
| A7.Red.40 | 39.7 (24.5-54.9) | 411 (272-550) |
| C.Red.40 | 7.39 (4.30-10.5) | 66.2 (28.7-104) |
| A7.Red.30 | 14.3 (6.60-22.0) | 199 (77.8-320) |
| C.Red.30 | 3.92 (1.62-6.20) | 12.4 (3.74-21.1) |
| NT.Red 40 | 4 (2.04-5.96) | 6.78 (1.04-12.5) |
| NT.Red.30 | 0.4 (0-1.08) | N/A |

The frequency of RFP+ cells per 100,000 cells (flow cytometry) or RFP+ cells per well given 150,000 cells seeded (hand counts), with mean and 95% confidence intervals (in parentheses), of HEK-293 transfections. The oligonucleotide transfections with both the I-SceI expression vector and the target plasmid are bolded. Cells were transfected with an I-SceI expression vector (pSce) and a target plasmid that contains the DsRed2 gene disrupted by two STOP codons and an I-SceI site. No DNA control, pSce only, pLDSLm only, and the oligos only negative controls were repeated 4 to 8 times. The 54 base homology containing oligonucleotide transfections using both plasmids (A7.Red.54 and C.Red.54) were repeated thirty-eight times, the oligonucleotides with 40 bases of homology (A7.Red.40 and C.Red.40) and the oligonucleotides with 30 bases of homology (A7.Red.30 and C.Red.30) were repeated 13 or 14 times, and the oligonucleotides that contained only homology with no 5' aptamer or non-binding control sequence (NT.Red.40 and NT.Red.30) were repeated 5 times. The flow cytometer was thought to be overreporting the number of RFP+ cells and hence underreporting the difference between the oligonucleotides with 30 bases of homology, as even the negative control samples contained some RFP+ cells according to the flow cytometer. Data presented in FIG. 5A.

In order to further validate the over-reporting of RFP+ cells by the flow cytometer, hand counts of the transfections were done. After seeding 150,000 cells, after 5 to 8 days the numbers of RFP+ cells were counted in each well. For the negative controls which were repeated 3 times each, no RFP+ cells were seen. The oligonucleotides with both the I-SceI expression vector and the target plasmid (shown bolded above) were repeated 12 to 14 times. Data presented in FIG. 5B.

Example 15

DsRed2 Digested pLDSLm Transfection Data

TABLE 11

| Transfected DNA | Flow Cytometry |
|---|---|
| No DNA | 2 (2-2) |
| Dig. pLDSLm | <0.5 (0-0) |
| A7.Red.54 | 1 (1-1) |
| C.Red.54 | 3 (3-3) |
| A7.Red.40 | 1 (1-1) |
| C.Red.40 | 4 (4-4) |
| A7.Red | 1 (1-1) |
| C.Red.30 | 1 (1-1) |
| A7.Red.54 | 737 (653-821) |
| C.Red.54 | 416 (265-567) |
| A7.Red.40 | 235 (124-346) |
| C.Red.40 | 144 (96.0-192) |
| A7.Red.30 | 143 (101-185) |
| C.Red.30 | 137 (86.3-188) |

The frequency of RFP+ cells per 100,000 cells (flow cytometry), with mean and 95% confidence intervals (in parentheses), of HEK-293 transfections. The oligonucleotide transfections with the target plasmid are bolded. Cells were transfected with a target plasmid that contained the DsRed2 gene disrupted by two STOP codons and an I-SceI site that was digested by I-SceI in vitro prior to transfection. No DNA control, I-SceI digested pLDSLm only, and the oligonucleotide only negative controls were repeated 1 to 2 times. The oligonucleotide transfections with the digested pLDSLm vector (bolded) were repeated 5 times. Data presented in FIG. 5C.

Example 16

Yeast Transformation in a rad52ΔBackground

TABLE 12

| Oligo | Break on Gal |
|---|---|
| No oligo (TRP5) | 2.14 (1.27-3.01) |
| A7.TRP5.54 | 3.06 (2.47-3.6) |
| C.TRP5.54 | 2.57 (1.73-3.42) |

The frequency of Trp+ colonies per $10^7$ viable cells, with mean and 95% confidence intervals (in parentheses), of yeast transformations in the FRO-155 strain from the BY4742 background with the ISceI gene and with the I-SceI site, except that the RAD52 gene has been deleted. 8 repeats of the no oligo control were done and 12 repeats for the A7.TRP5.54 and C.TRP5.54 oligonucleotides. Data presented in FIG. 10.

We claim:

1. A bifunctional oligonucleotide having 5' and 3' ends comprising:
   an aptamer on the 5' end of the bifunctional oligonucleotide that specifically binds to a DNA binding moiety, wherein the DNA binding moiety binds to a target DNA sequence; and
   donor polynucleotide sequence on the 3' end of the bifunctional oligonucleotide that is sufficiently complementary to the target DNA sequence to anneal to the target DNA sequence under physiological conditions and wherein the donor polynucleotide sequence repairs a double-stranded DNA break produced by the DNA binding moiety at or near the target DNA sequence, wherein the DNA binding moiety is a homing endonuclease selected from the group consisting of I-SceI, LAGLIDADG (SEQ ID NO:2) homing endonucleases, HNH endonuclease, His-Cys box enzymes, HNH (I-HmuI) endonuclease, His-Cys box (I-PpoI) endonuclease and GIY-YIG (I-TevI) endonuclease.

2. The bifunctional oligonucleotide of claim 1, wherein the homing endonuclease is I-SceI.

3. The bifunctional oligonucleotide of claim 1, wherein the target DNA sequence is a gene or fragment thereof.

4. The bifunctional oligonucleotide of claim 1, wherein the aptamer is a DNA aptamer.

5. The bifunctional oligonucleotide of claim 1, wherein the donor polynucleotide sequence is 90-100% homologous to the target DNA sequence.

6. The bifunctional oligonucleotide of claim 1, wherein the donor polynucleotide sequence is 100% complementary to the target DNA sequence.

7. A vector encoding the bifunctional oligonucleotide of claim 1.

8. A pharmaceutical composition comprising one or more bifunctional oligonucleotides according to claim 1.

9. The bifunctional oligonucleotide of claim 1, wherein the aptamer comprises DNA or RNA.

10. The bifunctional oligonucleotide of claim 1, wherein the donor polynucleotide sequence comprises DNA or RNA.

* * * * *